(12) United States Patent
Ward et al.

(10) Patent No.: US 8,784,439 B1
(45) Date of Patent: Jul. 22, 2014

(54) PERCUTANEOUS MEDICAL PROCEDURES AND DEVICES FOR CLOSING VESSELS USING MECHANICAL CLOSURES

(76) Inventors: Stephen V. Ward, Flagstaff, AZ (US); Kenneth Salce, Flagstaff, AZ (US); Matt D. Pursley, Alpharetta, GA (US); Joe E. Brown, Lilburn, GA (US)

( * ) Notice: Subject to any disclaimer, the term of this patent is extended or adjusted under 35 U.S.C. 154(b) by 0 days.

(21) Appl. No.: 13/413,156

(22) Filed: Mar. 6, 2012

Related U.S. Application Data

(62) Division of application No. 11/946,372, filed on Nov. 28, 2007, now abandoned.

(60) Provisional application No. 60/861,629, filed on Nov. 28, 2006.

(51) Int. Cl.
*A61B 17/12* (2006.01)
*A61B 17/064* (2006.01)
*A61B 17/06* (2006.01)
*A61B 17/00* (2006.01)
*A61B 17/03* (2006.01)

(52) U.S. Cl.
USPC .......... 606/158; 606/139; 606/151; 606/157; 606/213

(58) Field of Classification Search
USPC ......... 606/139–148, 151, 157–158, 219–220, 606/213, 232; 623/23.72; 128/898; 227/175.1, 176.1
See application file for complete search history.

(56) References Cited

U.S. PATENT DOCUMENTS

| | | | |
|---|---|---|---|
| 5,007,921 A * | 4/1991 | Brown | 606/221 |
| 5,709,224 A * | 1/1998 | Behl et al. | 128/898 |
| 5,865,791 A * | 2/1999 | Whayne et al. | 604/500 |
| 6,071,292 A * | 6/2000 | Makower et al. | 606/158 |
| 6,776,784 B2 * | 8/2004 | Ginn | 606/151 |
| 7,007,698 B2 * | 3/2006 | Thornton | 128/898 |
| 7,083,629 B2 * | 8/2006 | Weller et al. | 606/151 |
| 7,150,750 B2 * | 12/2006 | Damarati | 623/17.11 |
| 7,220,265 B2 * | 5/2007 | Chanduszko et al. | 606/139 |
| 7,306,614 B2 * | 12/2007 | Weller et al. | 606/151 |
| 7,413,570 B2 * | 8/2008 | Zamierowski | 606/215 |
| 7,427,279 B2 * | 9/2008 | Frazier et al. | 604/500 |
| 7,740,640 B2 * | 6/2010 | Ginn | 606/142 |
| 7,972,354 B2 * | 7/2011 | Prestezog et al. | 606/200 |
| 8,083,766 B2 * | 12/2011 | McGuckin, Jr. | 606/213 |
| 2001/0039426 A1 * | 11/2001 | Makower et al. | 606/153 |
| 2003/0208209 A1 * | 11/2003 | Gambale et al. | 606/144 |
| 2004/0122473 A1 * | 6/2004 | Ewers et al. | 606/222 |
| 2004/0267191 A1 * | 12/2004 | Gifford et al. | 604/22 |
| 2005/0021054 A1 * | 1/2005 | Ainsworth et al. | 606/143 |
| 2005/0192616 A1 * | 9/2005 | Callister et al. | 606/193 |
| 2005/0192629 A1 * | 9/2005 | Saadat et al. | 606/221 |
| 2005/0228407 A1 * | 10/2005 | Nobles et al. | 606/144 |
| 2005/0228475 A1 * | 10/2005 | Keeble et al. | 623/1.11 |
| 2006/0009798 A1 * | 1/2006 | Callister et al. | 606/200 |
| 2006/0282159 A1 * | 12/2006 | Taheri | 623/1.38 |
| 2007/0049968 A1 * | 3/2007 | Sibbitt et al. | 606/213 |
| 2007/0060895 A1 * | 3/2007 | Sibbitt et al. | 604/215 |
| 2007/0112425 A1 * | 5/2007 | Schaller et al. | 623/2.37 |
| 2007/0198058 A1 * | 8/2007 | Gelbart et al. | 606/213 |

* cited by examiner

*Primary Examiner* — Mark Mashack
(74) *Attorney, Agent, or Firm* — Jeffrey L. Thompson; Thompson & Thompson, P.A.

(57) ABSTRACT

Percutaneous medical procedures are provided, which use endovascular instruments to install mechanical closures for closing vessels, such as veins. The mechanical closures can be one or more sutures that are anchored to the vessel walls and then cinched to closed the vessel. The mechanical closures can also be resilient clips or stents that are expanded within the vessel to pierce the vessel walls, and are then contracted to pull the vessel closed. Various techniques for installing the mechanical closures are also described.

7 Claims, 41 Drawing Sheets

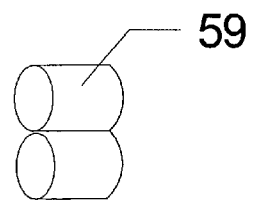
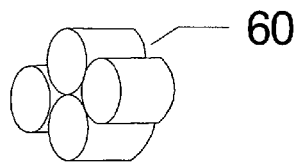
Fig. 33         Fig. 34
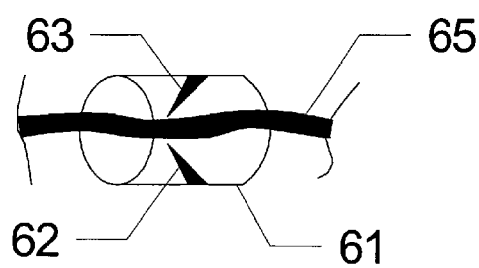
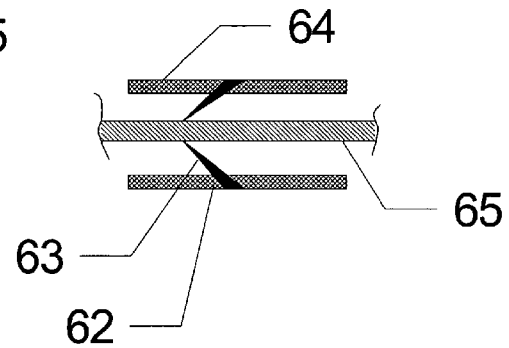
Fig. 35         Fig. 36
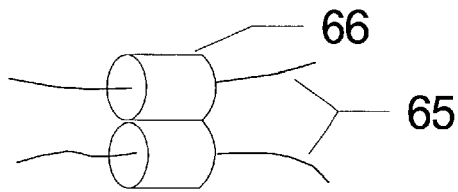
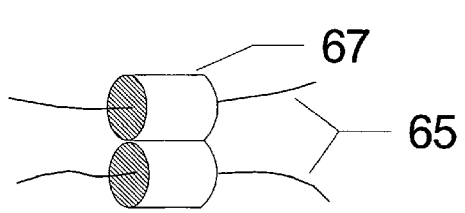
Fig. 37         Fig. 38

PERCUTANEOUS MEDICAL PROCEDURES AND DEVICES FOR CLOSING VESSELS USING MECHANICAL CLOSURES

RELATED APPLICATIONS

This application is a divisional of U.S. application Ser. No. 11/946,372 filed on Nov. 28, 2007 now abandoned, and claims priority of U.S. Provisional Application No. 60/861,629 filed on Nov. 28, 2006. The entire contents of these prior applications are incorporated herein by reference.

BACKGROUND OF THE INVENTION

1. Field of the Invention

The present invention relates generally to percutaneous medical procedures and devices that can be used to close vessels, such as veins, and particularly to procedures and devices that close vessels by installing mechanical closures, such as sutures and/or clips.

2. Description of the Related Art

Percutaneous treatment of lower extremity venous insufficiency is a new, rapidly progressive part of interventional radiology practice. The prevalence of venous related diseases far exceeds that of arterial diseases. A variety of treatment options are used by interventional radiologists to treat venous insufficiency.

The current treatment options include endovascular laser, sclerotherapy, and phlebectomy. In many cases, however, these treatment options are not optimal. The current modalities are particularly suboptimal in treatment of incompetent perforator veins. The incompetent perforator veins are not candidates for laser therapy. Because the veins feed directly into the deep venous system, sclerotherapy is often suboptimal and dangerous. Other veins also are not ideal for conventional therapy due to the proximity to adjacent structures and due to patient related issues.

There is a need in the industry for improved percutaneous procedures for safely and rapidly closing veins and other vessels.

BRIEF DESCRIPTION OF THE DRAWINGS

The present invention will become more clearly appreciated as the disclosure of the present invention is made with reference to the accompanying drawings. In the drawings:

FIG. 2 shows a step of the medical procedure in which a suture needle is straightened within a suture guide.

FIG. 3 shows the suture needle and suture guide being inserted into a vessel.

FIG. 4 shows the suture needle advanced out the distal end of the suture guide and through the vessel wall at a treatment location.

FIG. 5 shows a suture with a first anchor at its distal end loaded into a push tube.

FIG. 6 shows the suture and push tube being inserted into the lumen of the suture needle.

FIG. 7 shows the suture and first anchor advanced through the vessel wall out of the distal end of the suture needle.

FIG. 8 shows the suture needle retracted back into the suture guide leaving the suture and first anchor anchored in the vessel wall.

FIG. 9 shows the suture needle rotated 180 degrees and advanced through the vessel wall a second time with the suture pulled through the vessel wall at a second location.

FIG. 10 shows a sliding suture anchor being inserted into the suture needle using the push tube.

FIG. 11 shows the sliding suture anchor after it is advanced through the suture needle and expanded outside of the vessel wall.

FIG. 12 shows the procedure after the suture needle is retracted back through the suture guide leaving the suture and second anchor anchored in the vessel wall.

FIG. 13 shows the suture being used to cinch the vessel closed.

FIG. 14 shows a cinch ring being installed to keep the suture in its cinched condition.

FIG. 15 shows a step in the medical procedure in which a suture needle is advanced out the distal end of the suture guide and through the vessel wall at a treatment location.

FIG. 16 shows the suture guide after the suture needle has been fully retracted leaving a first suture and first anchor anchored in the vessel wall at a first location.

FIG. 17 shows the suture needle rotated 180 degrees and reinserted back into the suture guide and advanced through the vessel wall a second time.

FIG. 18 shows the suture guide after the suture needle has been fully retracted again leaving a second suture and second anchor anchored in the vessel wall at a second location.

FIG. 19 shows a multiple lumen cinch ring being installed over the first and second sutures.

FIG. 20 shows an alternative single lumen cinch ring structure.

FIG. 21 shows the cinch ring advanced over the first and second sutures to a point near the treatment location.

FIG. 22 shows the sutures being used to cinch the vessel closed with the cinch ring installed to maintain the cinched condition.

FIG. 33 shows a multiple lumen cinch ring for use in the present invention.

FIG. 34 shows another multiple lumen cinch ring for use in the present invention.

FIG. 35 shows a single lumen cinch ring having a directional biasing structure.

FIG. 36 is a cross section side view of the single lumen cinch ring shown in FIG. 35.

FIG. 37 shows a multiple lumen cinch ring that is crimped or clamped over the suture.

FIG. 38 shows a multiple lumen cinch ring that can be fixed in place by applying heat.

FIG. 39 shows a polymeric or metallic tube from which the anchor device is constructed.

FIG. 40 shows the tube of FIG. 39 after one end thereof has been split to form an expandable portion.

FIG. 41 shows the tube of FIG. 40 with the split end flared by a heated die.

FIG. 42 is a cross sectional view of the anchor device showing a directional biasing structure extending into a lumen thereof.

FIG. 43 shows the anchor device contracted within a suture needle for deployment through a vessel wall.

FIG. 43a shows the anchor device in its deployed condition against a vessel wall.

FIG. 44 shows an isometric view of the expandable suture anchor device.

FIG. 45 shows a top view of the suture anchor device.

FIG. 46 shows a side view of the suture anchor device in its expanded condition.

FIG. 47 shows a side view of the suture anchor device in its compressed condition.

FIG. 60 shows a suture needle with a distal tip.

FIG. 61 is a detail cross section view of the suture needle distal tip without a stylet.

FIG. 62 is a detail cross section view of the suture needle distal tip with a stylet that does not exit the needle.

FIG. 63 is a detail cross section view of the suture needle distal tip with a stylet that is exposed and used to pre-penetrate the vessel wall.

FIGS. 64 and 65 are detail cross section views of suture needle distal tips with stylets that are matched to conical cuts on the suture needles.

FIG. 66 shows the insertion of a first clip having an attached suture to a treatment location within a vessel.

FIG. 67 shows the first clip attached to the vessel wall.

FIG. 68 shows a second clip attached to the vessel wall with the suture extending between the first and second slips.

FIG. 69 shows the suture being cinched to close the vessel.

FIG. 72 shows a suture needle straightened within a suture guide and being inserted into a vessel.

FIG. 73 shows the suture needle advanced out the distal end of the suture guide and through the vessel wall at a treatment location.

FIG. 74 shows a first suture with a first T-bar anchor at its distal end loaded into a push tube.

FIG. 75 shows the first suture and push tube being inserted into the lumen of the suture needle.

FIG. 76 shows the first suture and first T-bar anchor advanced through the vessel wall out of the distal end of the suture needle.

FIG. 77 shows the suture needle retracted back into the suture guide leaving the first suture and first T-bar anchor anchored in the vessel wall.

FIG. 78 shows the suture needle rotated 180 degrees and reinserted back into the suture guide and advanced through the vessel wall a second time.

FIG. 79 shows the suture guide after the suture needle has been fully retracted again leaving a second suture and second anchor anchored in the vessel wall at a second location.

FIG. 80 shows a cinch ring being inserted into the suture guide.

FIG. 81 shows the cinch ring installed over the first and second sutures and being used to cinch the vessel closed.

FIG. 82 shows the cinched vessel after the suture guide and other instrument components are removed from the vessel.

DETAILED DESCRIPTION OF THE INVENTION

Figure 104:
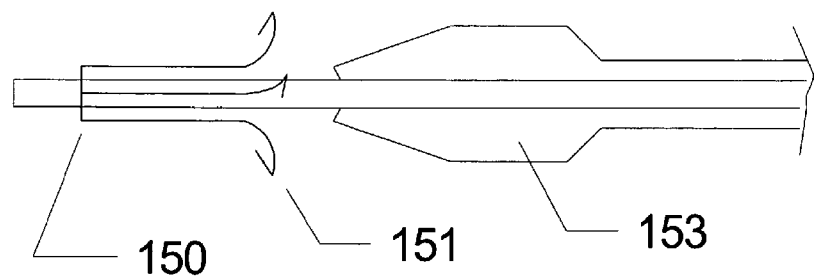
FIG. 104 shows the barbed stent of FIG. 100 with an alternative mechanical expander for use in installing the stent to close a vessel.

Percutaneous medical procedures and devices used therefor according to embodiments of the present invention will now be described in detail with reference to FIGS. 1 to 104 of the accompanying drawings.

FIGS. 1 to 14 illustrate a first embodiment of the present invention. In the first embodiment, an endovascular instrument 10 is used in a percutaneous medical procedure to install a mechanical closure 11 comprising a single suture 12 for closing a vessel 13. As used in the present application, the term "vessel" should be understood to include any hollow anatomical structure, including, without limitation, veins, arteries, gastric structures, coronary structures, pulmonary structures, tubular structures associated with reproductive organs, and the like.

Figure 1:
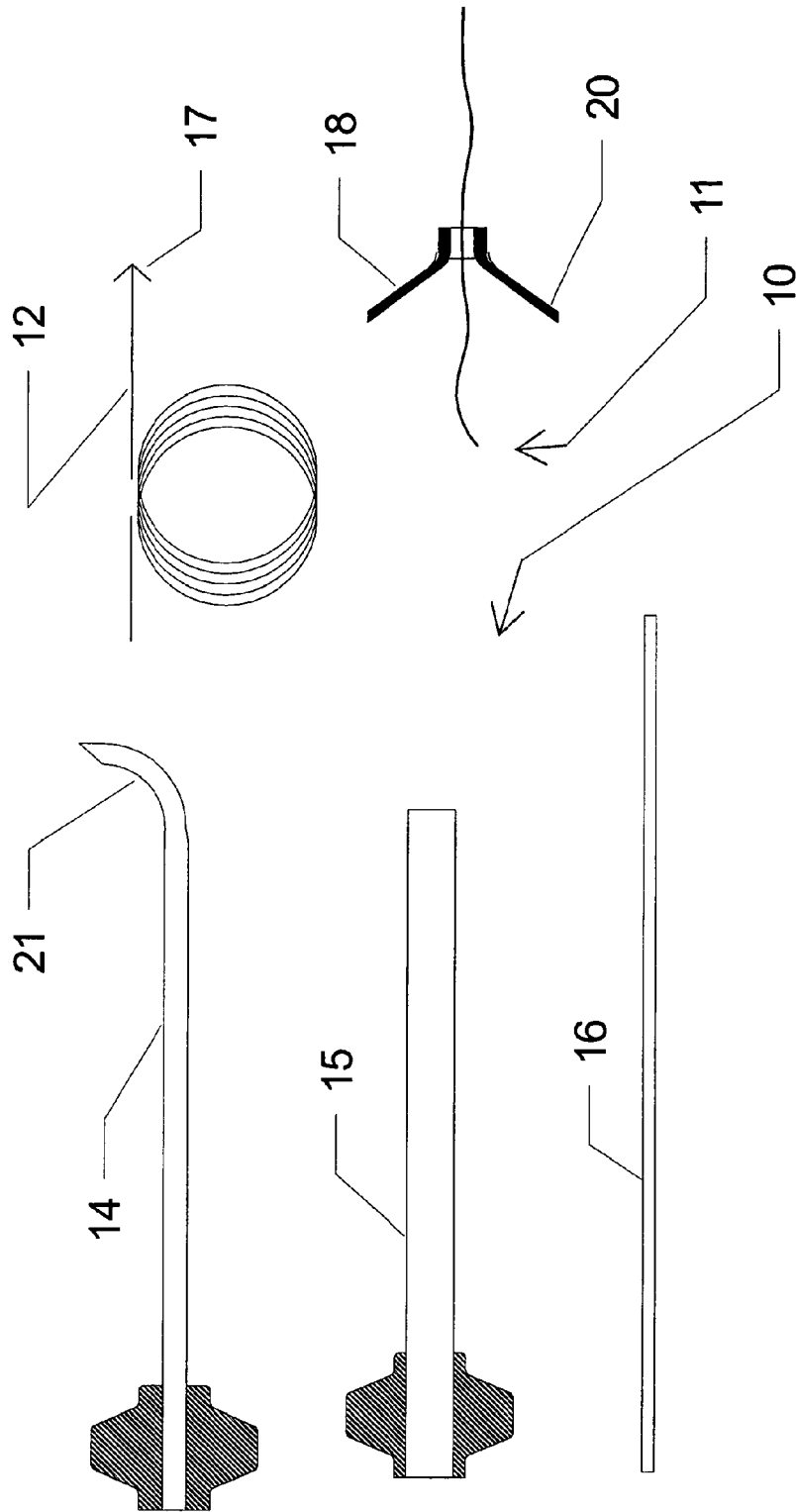
FIG. 1 shows the various components of an endovascular instrument and device for installing a suture in a percutaneous medical procedure according to the present invention.

The various components of the endovascular instrument 10 and mechanical closure 11 are shown in FIG. 1. The instrument 10 includes a suture needle 14, a suture guide 15, and a suture push tube 16. The mechanical closure 11 includes the suture 12 with a first expanding anchor 17 fixed at the distal end of the suture 12, and a second expanding anchor 18 that can be slid along the suture 12.

The suture needle 14 is a flexible polymeric or metallic needle. The suture needle 14 can be used to penetrate a wall 19 of the vessel 13, inject fluid media, and insert the suture 12 and expanding anchors 17 and 18. The suture needle 14 has a preset curve in its distal portion 21.

The suture guide 15 is a wire reinforced guide catheter. The suture guide 15 is used to advance the suture needle 14 to the treatment location and to cinch the suture 12.

The suture push tube 16 is a polymeric or metallic catheter. The suture push tube 16 is used to advance the suture 12 and anchors 17, 18 through the suture needle 14.

The first and second anchors 17, 18 are polymeric or metallic devices with deflectable legs 20. The legs 20 of the anchors 17, 18 can be deflected into a closed position in which the legs 20 fold flat against the suture 12 to allow the anchors 17, 18 to be passed through the suture needle 14 during the procedure. After the anchors 17, 18 pass through the suture needle 14, the legs 20 expand to their original position. Various configurations of anchors 17, 18 and T-bars (described below) can be used in the present invention for attaching sutures 12 to the vessel wall 19.

Figure 2:
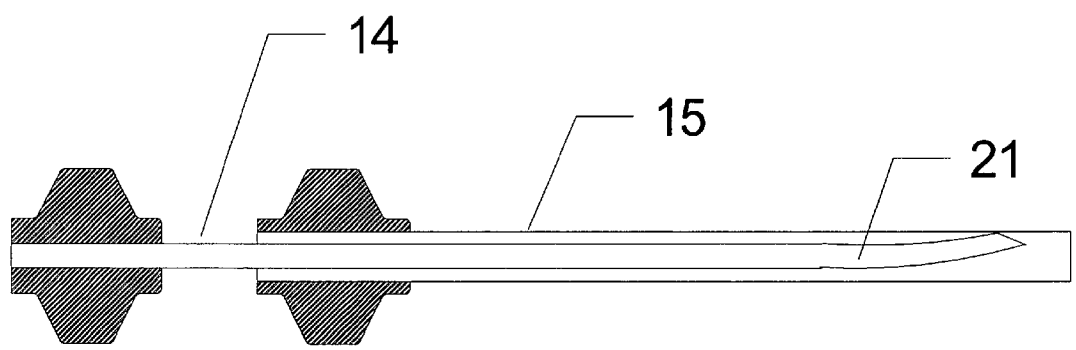
FIGS. 2 to 14 show a series of steps for performing a percutaneous medical procedure for closing a vessel using the instrument shown in FIG. 1 to install a single suture.
Figure 3:
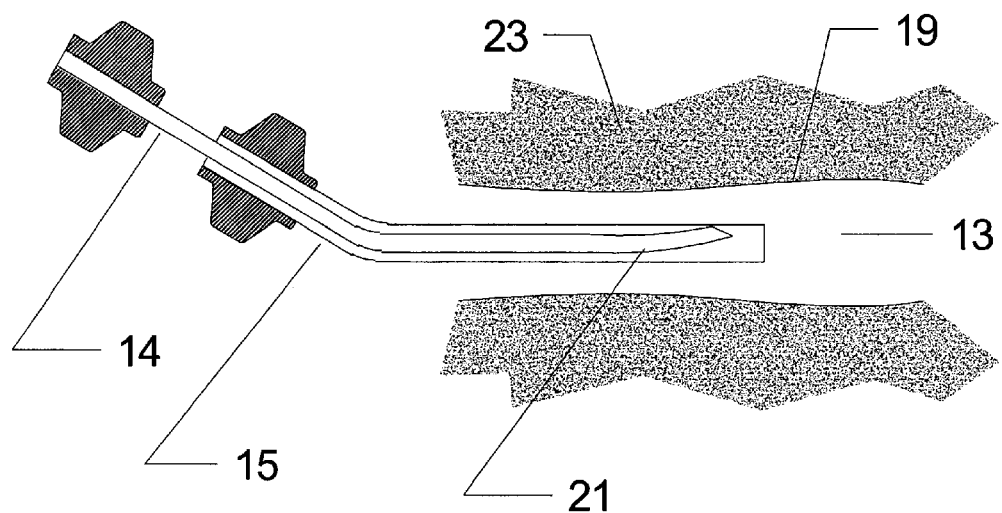
Figure 4:
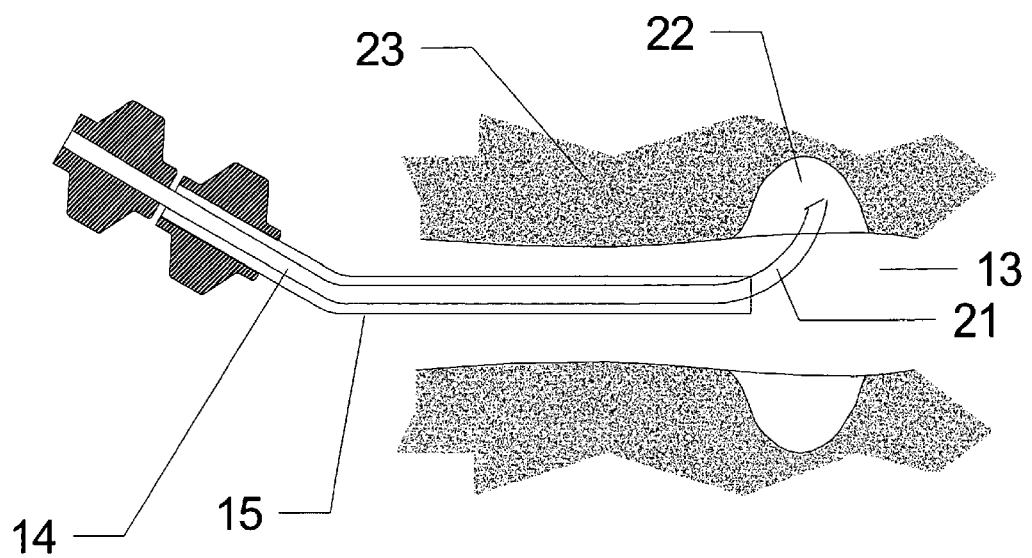

FIGS. 2 to 14 show a series of steps for performing the percutaneous medical procedure for closing a vessel 13 using the instrument 10 shown in FIG. 1 to install a single suture 12. The suture needle 14 is inserted into the suture guide 15, as shown in FIG. 2, so that the preset curve in the distal portion 21 of the suture needle 14 is straightened within the suture guide 15. The assembly of the suture guide 15 and the suture needle 14 is then inserted into the vessel 13 to a desired treatment location (closure point), as shown in FIG. 3. The suture needle 14 is then advanced within the suture guide 15 until the distal portion 21 of the suture needle exits the suture guide, and the preset curve in the distal portion 21 causes the suture needle 14 to curve toward the vessel wall 19. The suture needle 14 continues to be advanced until its distal tip penetrates through the vessel wall 19 at a first location, as shown in FIG. 4.

A fluidic media 22, such as saline, is injected through the suture needle 14 after the needle 14 penetrates through the vessel wall 19. The fluidic media 22 surrounds the vessel 13 and isolates the vessel 13 from surrounding tissue 23. The fluidic media 22 also imparts a closing pressure on the vessel 13, which can facilitate the closing procedure. The fluidic media 22 can also be injected externally using a conventional needle and syringe, and can be injected prior to the suture needle 14 penetrating the vessel wall 19.

Figure 5:
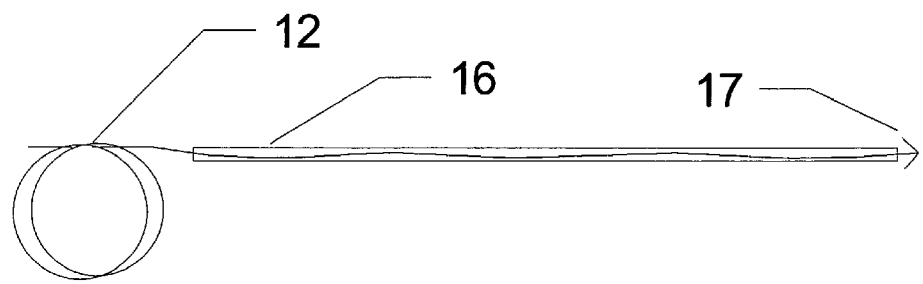
Figure 6:
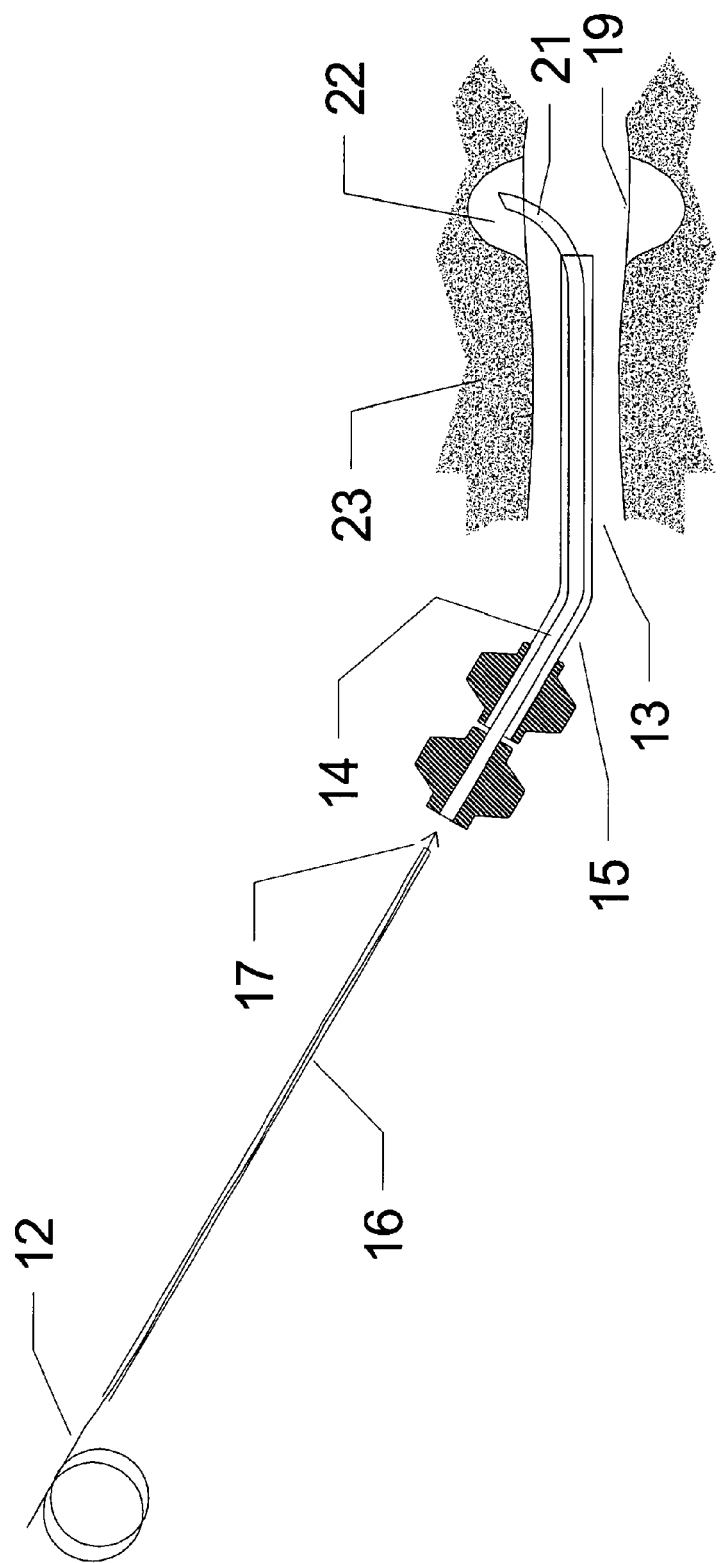
Figure 7:
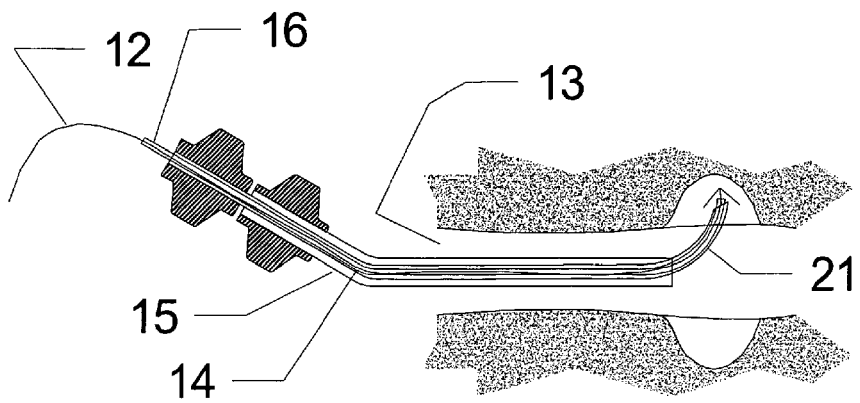

The suture 12 with the first expanding anchor 17 fixed at its distal end is then loaded into the suture push tube, as shown in FIG. 5. The push tube 16 with the suture 12 and the first expanding anchor 17 are then inserted into the lumen of the suture needle 14, as shown in FIG. 6. The diameter of the lumen of the suture needle 14 is smaller than the expanded size of the first expanding anchor 17, so that the anchor 17 has to be contracted as it passes into and through the suture needle 14. The push tube 16 is advanced through the suture needle 14, along with the suture 12 and first expanding anchor 17, until the suture 12 and first expanding anchor 17 exit the distal end of the suture needle 14 into the fluidic media 22 surrounding the vessel 13, as shown in FIG. 7. The first expanding anchor 17 expands into its original expanded shape upon exiting the suture needle 14.

Figure 8:
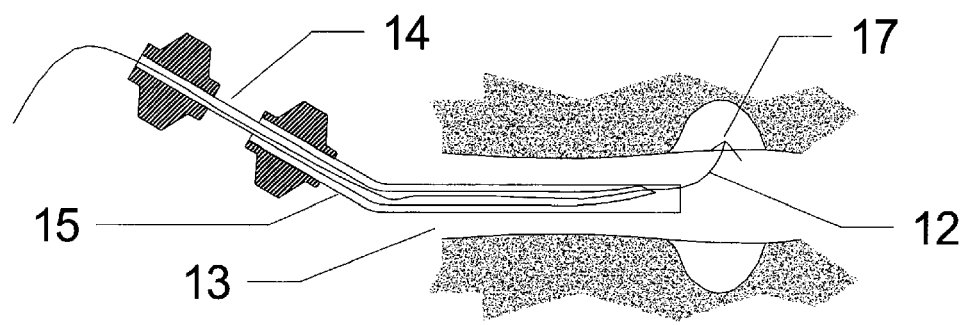

The push tube 16 is then removed from the suture needle 14, and the suture needle 14 is retracted into the suture guide 15 leaving the suture 12 and the first expanding anchor 17 anchored in the vessel wall 19, as shown in FIG. 8. Upon retraction into the suture needle 14, the distal portion 21 of the suture needle 14 is again straightened within the suture guide 15.

Figure 9:
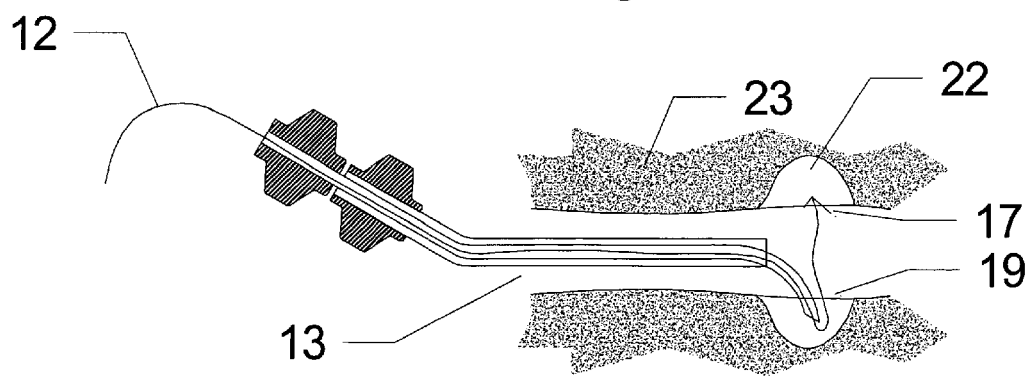

The suture needle 14 is then rotated about its longitudinal axis (e.g., 180 degrees), and then advanced within the suture guide 15 until the distal portion 21 of the suture needle 14 exits the suture guide 15 and curves toward the vessel wall 19. The suture needle 14 continues to be advanced until its distal tip penetrates the vessel wall 19 at a second location angularly spaced from the first location, as shown in FIG. 9. The suture 12 is pulled through the vessel wall 19 along with the distal tip of the suture needle 14. A second injection of fluidic media 22 through the suture needle 14 can be made at this time to help isolate the second location of the vessel wall 19 from the surrounding tissue 23, although the first injection described above will likely be sufficient.

Figure 10:
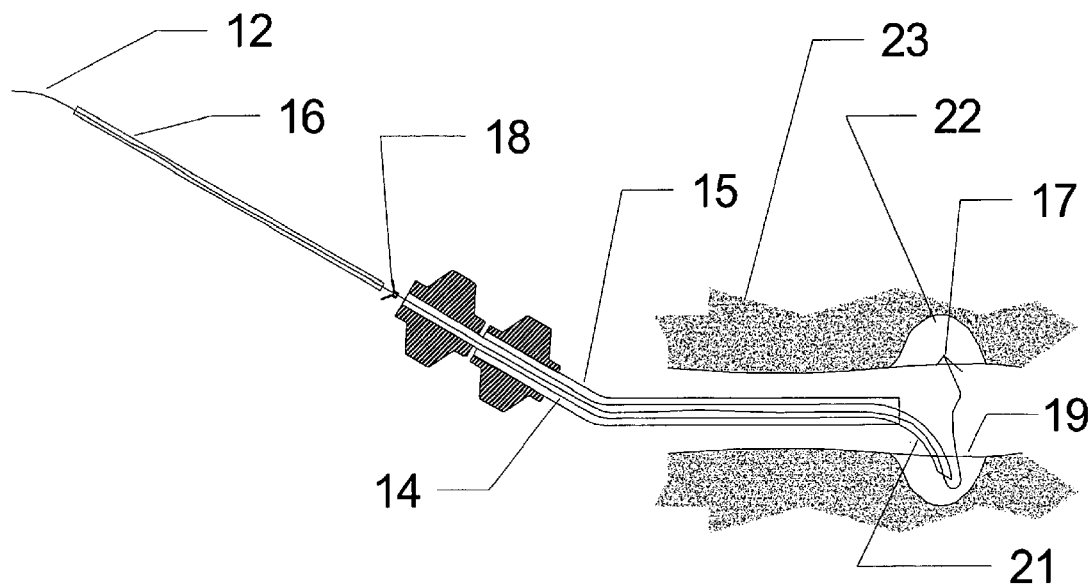
Figure 11:
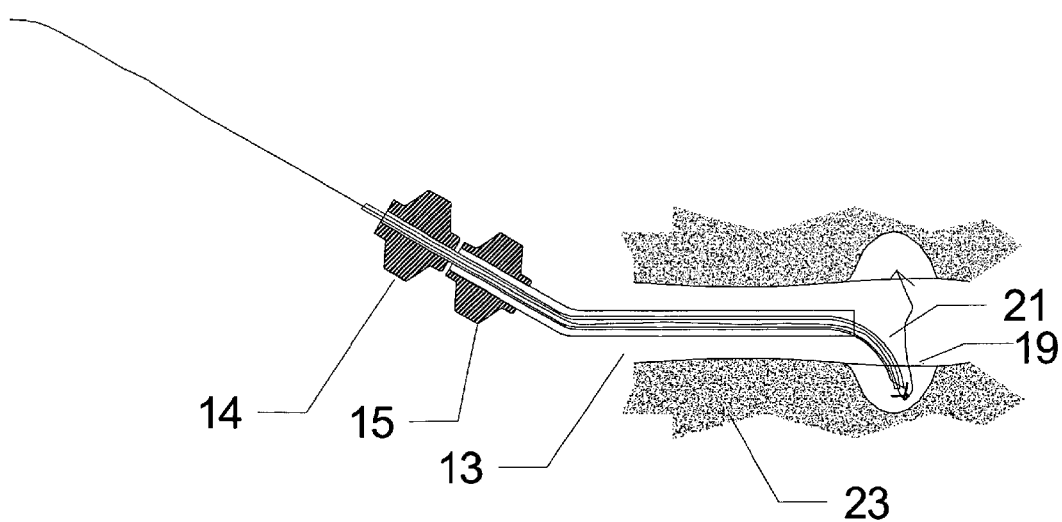

The second expanding anchor 18 is then slid over the suture 12, and the push tube 16 is loaded onto the suture 12 behind the second anchor 18, as shown in FIG. 10. The push tube 16 is used to push the second expanding anchor 18 into the suture needle 14. The second anchor 18 is contracted as it passes into and through the suture needle 14. The second anchor 18 is advanced through and out of the suture needle 14 using the push tube 16, as shown in FIG. 11.

Figure 12:
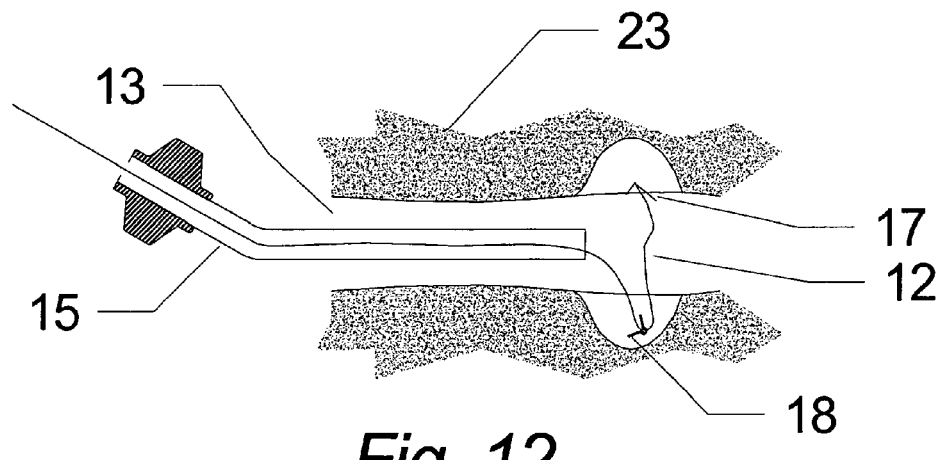
Figure 13:
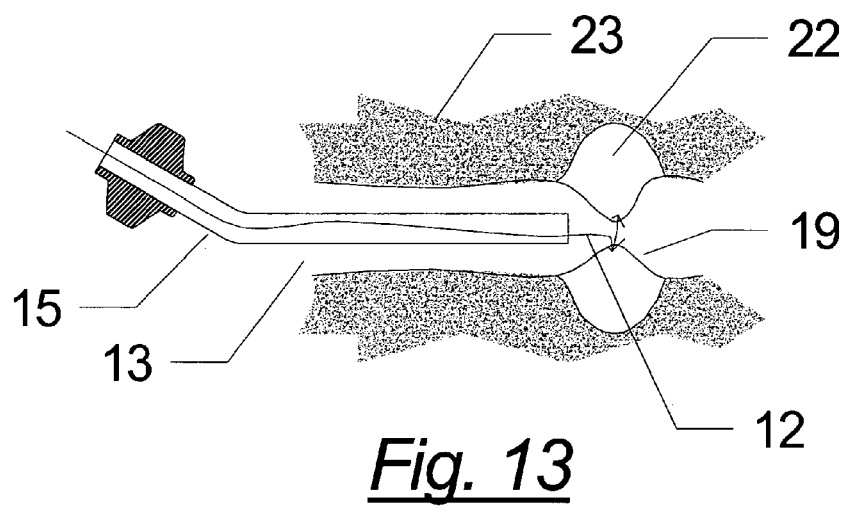

The suture needle 14 and push tube 16 are then retracted and removed from the suture guide 15, leaving behind the suture 12 and the first and second expanding anchors 17, 18, as shown in FIG. 12. The suture 12 is then pulled back into the suture guide 15, which causes the first and second anchors 17, 18 to come together and close the vessel 13, as shown in FIG. 13.

Figure 14:
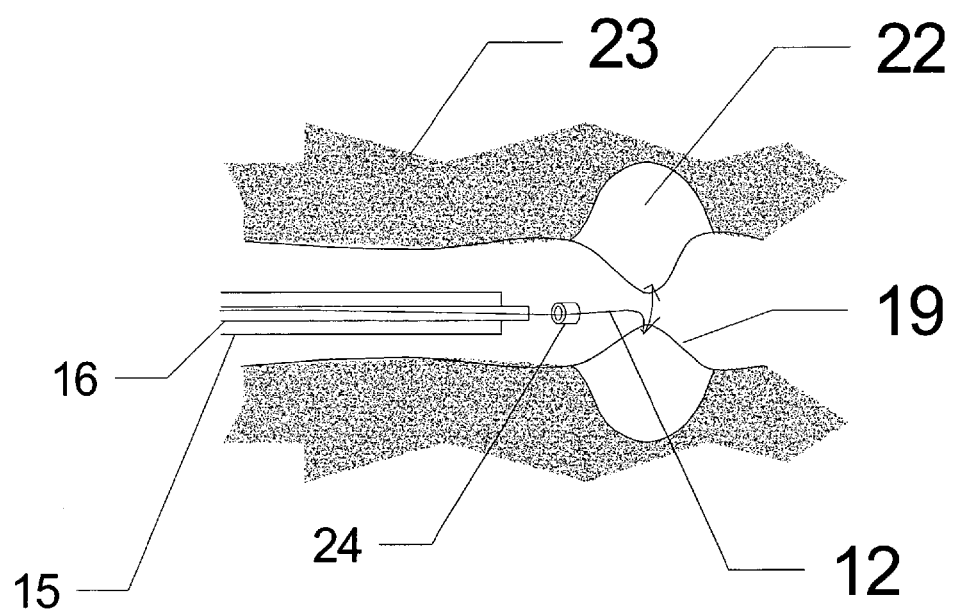

A cinch mechanism 24, such as a cinch ring with a single lumen and a directional biasing structure, is slid over the suture 12 and pushed through the suture guide 15 and into position using a push tube 16, as shown in FIG. 14. The cinch mechanism 24 functions to prevent the suture 12 from loosening and allowing the vessel 13 to reopen. The cinch mechanism 24 can also serve to hold or guide the suture 12 as it is tightened to close the vessel 13. Various types of cinch mechanisms contemplated by the present invention are illustrated in the drawings and are further described below.

A second embodiment of the present invention will now be described with reference to FIGS. 15 to 22. In the second embodiment, an endovascular instrument 10 is used to install a mechanical closure comprising a plurality of sutures 31, 32 for closing a vessel 13. The various components of the endovascular instrument 10 are generally the same as those used in the first embodiment and illustrated in FIG. 1. However, the sutures 31, 32 and anchors 33, 34 in this embodiment are different from those described above in the first embodiment.

Figure 15:
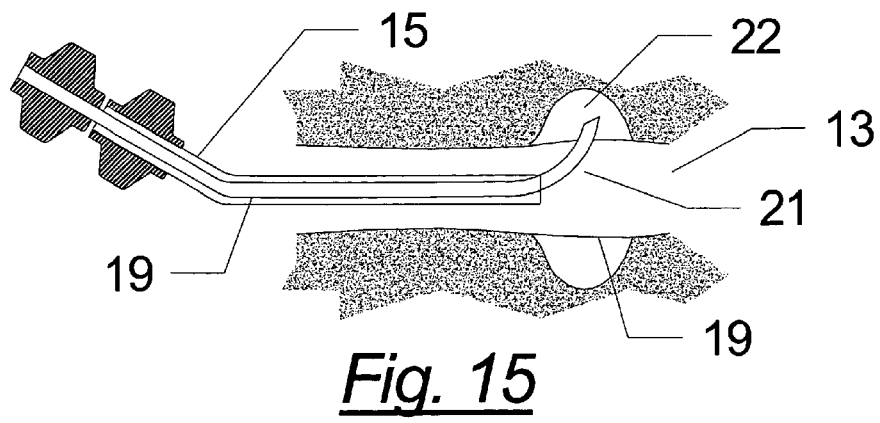
FIGS. 15 to 22 show a series of steps for performing a percutaneous medical procedure for closing a vessel by installing multiple sutures.

In the procedure according to the second embodiment, the suture needle 14 is inserted into the suture guide 15, similar to that shown in FIG. 2, so that the preset curve in the distal portion 21 of the suture needle 14 is straightened within the suture guide 15. The assembly of the suture guide 15 and the suture needle 14 is then inserted into the vessel 13 to a desired treatment location (closure point), similar to that shown in FIG. 3. The suture needle 14 is then advanced within the suture guide 15 until a distal portion 21 of the suture needle 14 exits the suture guide 15, and the preset curve in the distal portion 21 causes the suture needle 14 to curve toward the vessel wall 19. The suture needle 14 continues to be advanced until its distal tip penetrates through the vessel wall 19 at a first location, as shown in FIG. 15.

A fluidic media 22, such as saline, is injected through the suture needle 14 after the needle penetrates through the vessel wall 19. The fluidic media 22 surrounds the vessel 13 and isolates the vessel wall 19 from surrounding tissue 23. The fluidic media 22 also imparts a closing pressure on the vessel 13, which can facilitate the closing procedure. As mentioned above, the fluidic media 22 can also be injected externally using a conventional needle and syringe, and can be injected prior to the suture needle 14 penetrating the vessel wall 19.

A first suture 31 with a first expanding anchor 33 fixed at its distal end is then loaded into the suture push tube 16, inserted into the lumen of the suture needle 14, and advanced through the suture needle 14 until the first expanding anchor 33 exits the distal end of the suture needle 14 into the fluidic media 22 surrounding the vessel 13. This portion of the procedure is the same as in the first embodiment and illustrated in FIGS. 5 to 7. The first expanding anchor 33 expands into its original expanded shape outside the vessel wall 19 upon exiting the suture needle 14.

Figure 16:
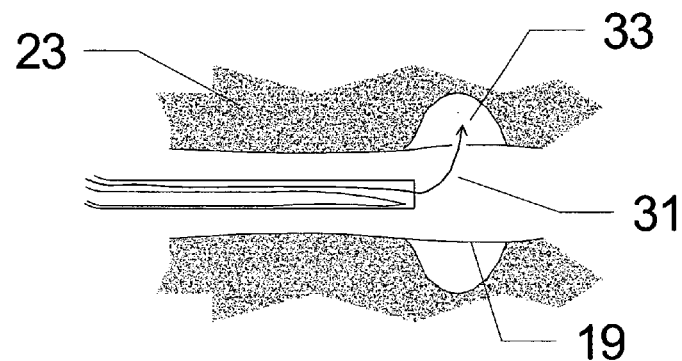
Figure 17:
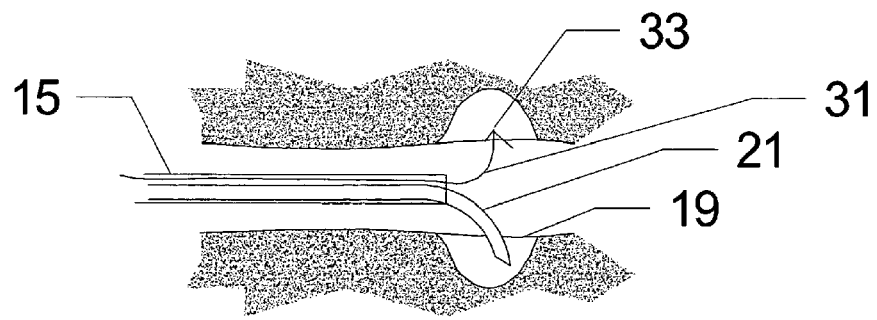

The push tube 16 and suture needle 14 are then retracted and removed from the suture guide 15 leaving the first suture 31 and the first expanding anchor 33 anchored in the vessel wall 19, as shown in FIG. 16. After the suture needle 14 is removed from the suture guide 15 and slid off of the first suture 31, the suture needle 14 is reinserted into the suture guide 15. Before advancing the suture needle 14 out of the distal end of the suture guide 15, the suture needle 14 is rotated about its longitudinal axis (e.g., 180 degrees). The suture needle 14 is then advanced within the suture guide 15 until the distal portion 21 of the suture needle 14 exits the suture guide 15 and curves toward the vessel wall 19. The suture needle 14 continues to be advanced until its distal tip penetrates the vessel wall 19 at a second location angularly spaced from the first location, as shown in FIG. 17.

A second suture 32 with a second expanding anchor 34 fixed at its distal end is then loaded into the suture push tube 16, inserted into the lumen of the suture needle 14, and advanced through the suture needle 14 until the second expanding anchor 34 exits the distal end of the suture needle 14 into the fluidic media 22 surrounding the vessel 13. The second expanding anchor 34 expands into its original expanded shape outside the vessel wall 19 upon exiting the suture needle 14.

Figure 18:
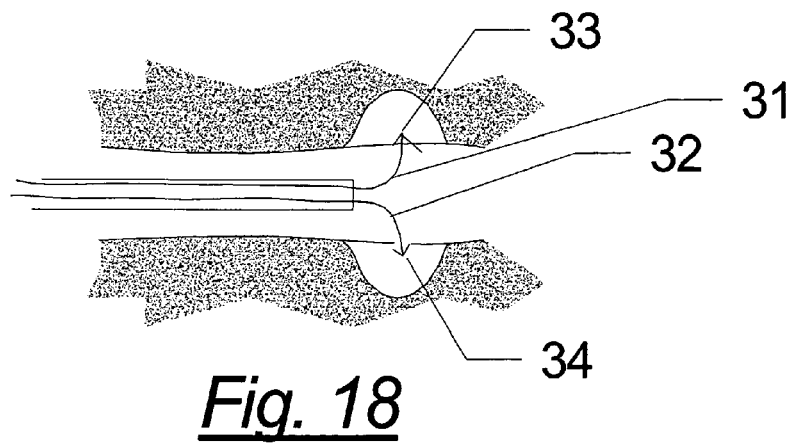
Figure 19:
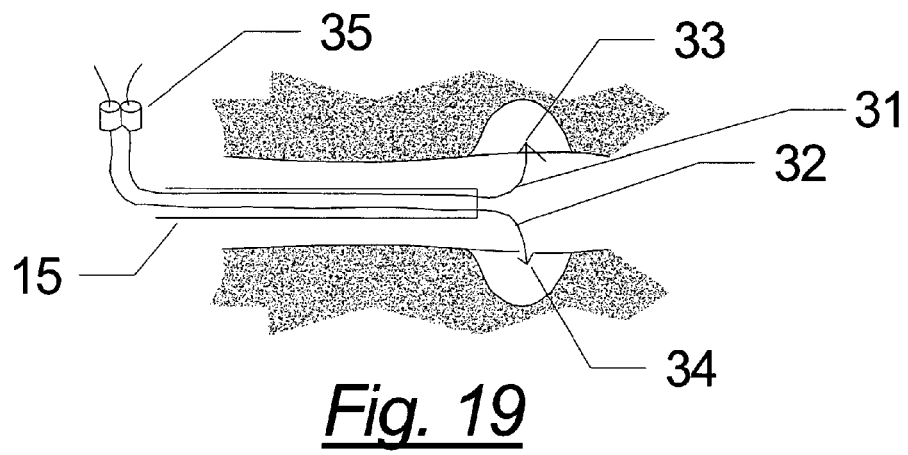
Figure 20:
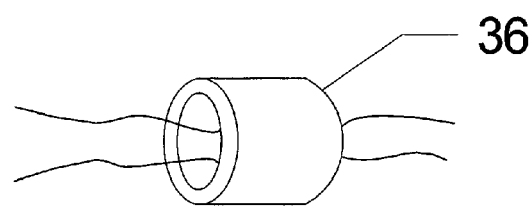

The push tube 16 and suture needle 14 are then retracted and removed from the suture guide 15 leaving the second suture 32 and the second expanding anchor 34 anchored in the vessel wall 19, as shown in FIG. 18. These steps can be repeated, if desired, to install additional sutures with expanding anchors fixed at their distal ends. Multiple sutures can also be installed along the length of the vessel 13.

Figure 21:
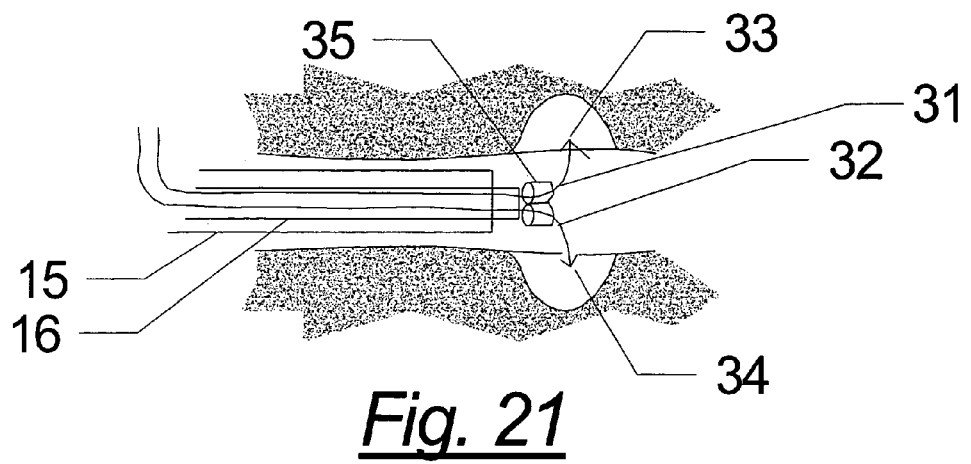
Figure 22:
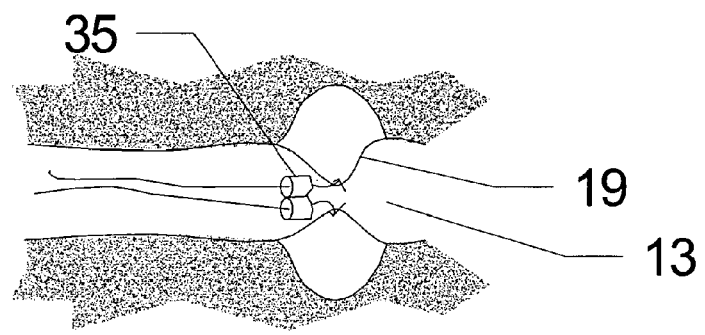

A cinch mechanism, such as a cinch ring 35 with multiple lumens (FIG. 19) or a cinch ring 36 with a single lumen (FIG. 20), is slid over the first and second sutures 31, 32 (and the additional sutures, if any) and pushed through the suture guide 15 and into position using the push tube 16, as shown in FIG. 21. The cinch mechanism 35, 36 is used in conjunction with the sutures 31, 32 to pull the vessel 13 closed and keep it closed, as shown in FIG. 22. A direction biasing structure (described below) can be provided within the cinch mechanism 35, 36 to keep the cinch mechanism 35, 36 in place on the sutures 31, 32. Various types of cinch mechanisms are illustrated in the drawings and described below.

Figure 23:
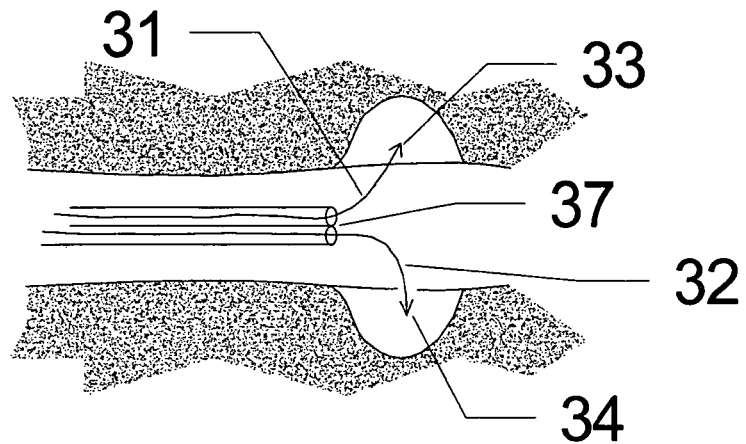
FIG. 23 shows a multiple lumen suture guide for installing multiple sutures using the method steps shown in FIGS. 15 to 22, or by using two suture needles simultaneously.

The procedure described above and shown in FIGS. 15 to 22 uses a single lumen suture needle 14. FIG. 23 shows a multiple lumen suture guide 37 that can be used in this procedure. The multiple lumen suture guide 37 can be used with a single suture needle 14 that passes through one lumen at a time, or it can be used with two suture needles simultaneously.

Figure 24:
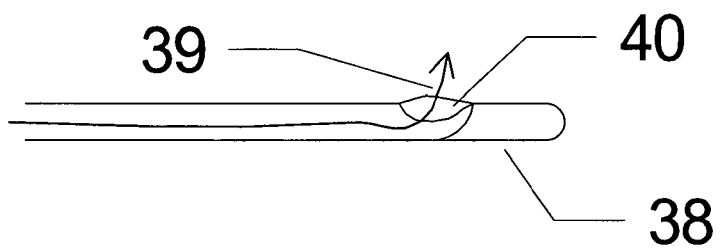
FIG. 24 shows a single lumen side port catheter for installing sutures in a percutaneous medical procedure according to the present invention.

FIG. 24 shows a single lumen side port catheter 38 for installing sutures 39 in a percutaneous medical procedure according to the present invention. The side port catheter 38 can be used as the suture guide to perform the procedures described above using a suture needle (not shown) without a preset curve at its distal end. In this case, the side port 40 of the catheter 38 causes the suture needle to curve toward the wall of the vessel upon exiting the catheter 38. The suture needle can be retracted into the catheter 38 and the entire catheter 38 rotated to reposition the side port 40 and direct the suture needle toward the desired locations on the vessel wall.

Figure 25:
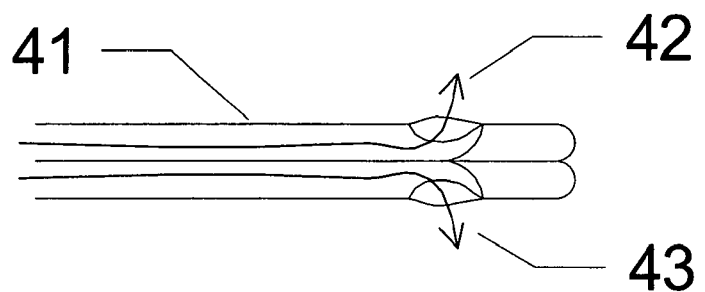
FIG. 25 shows a multiple lumen side port catheter for installing sutures in a percutaneous medical procedure according to the present invention.

FIG. 25 shows a multiple lumen side port catheter 41 for installing sutures 42, 43 in a percutaneous medical procedure according to the present invention. The multiple lumen side port catheter 41 can be used with a single suture needle that passes through one lumen at a time, or it can be used with two suture needles simultaneously. The multiple lumen side port catheter 41 can be used in a manner similar to the multiple lumen suture guide 37 shown in FIG. 23, except that suture needles without preset curves at their distal ends will be used.

Figure 26:
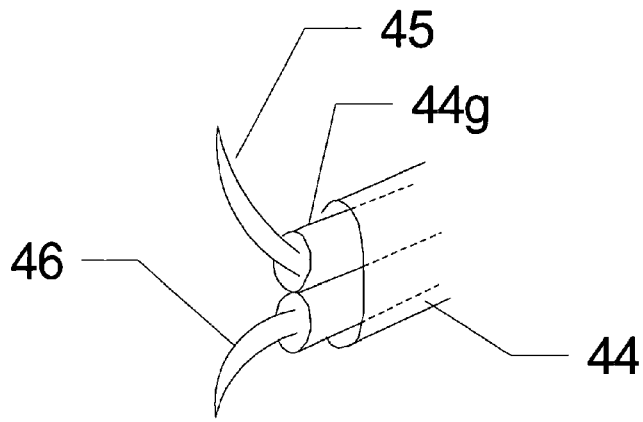
FIG. 26 is a perspective view of a shows a multiple lumen suture guide having two suture needles extending from the distal end thereof.
Figure 27:
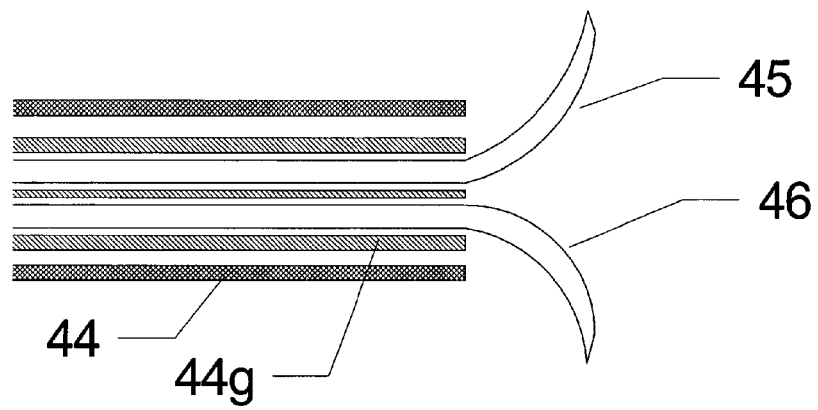
FIG. 27 is a cross section side view of the instrument shown in FIG. 26.

FIGS. 26 and 27 show a device 44 having a multiple lumen suture guide 44g having two suture needles 45, 46 extending from the distal end thereof. The two suture needles 45, 46 in this embodiment can be connected at their proximal ends to maintain the desired orientation relative to each other for simultaneous advancement through the suture guide 44. Alternatively, the two needles 45, 46 can be kept separate and operated independently of each other to install the sutures in the vessel wall.

Figure 28:
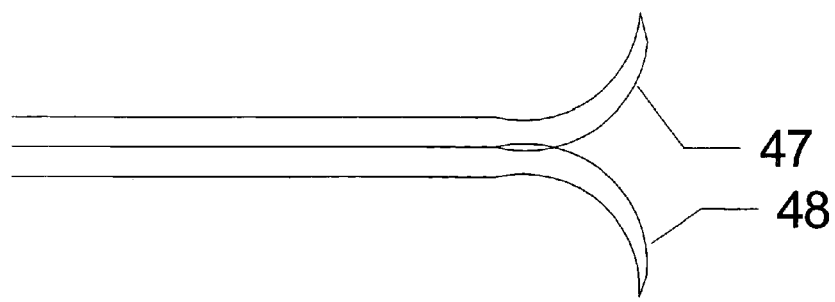
FIG. 28 is a side view of a suture needle assembly in which two suture needles are joined together for insertion through a single lumen.

FIG. 28 shows another variation where two suture needles 47, 48 are joined together at their midpoints or near their distal ends for insertion into a single lumen suture guide. The two joined suture needles can be used simultaneously to install sutures in opposing sides of a vessel wall.

Figure 29:
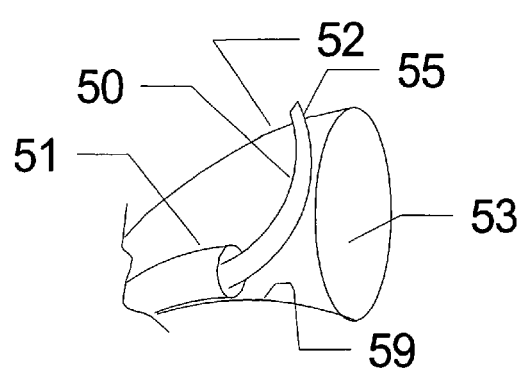
FIG. 29 shows a single suture needle being used with a suture guide to penetrate a vessel wall.
Figure 30:
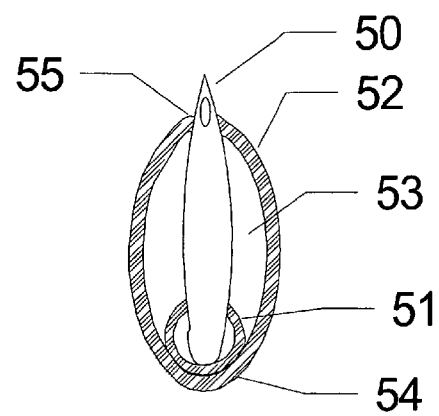
FIG. 30 shows an end view of the assembly shown in FIG. 29.

FIGS. 29 and 30 show a single suture needle 50 being used with a suture guide 51 to penetrate a wall 52 of a relatively large vessel 53. As seen in these figures, the suture guide 51 tends to be pushed against one side 54 of the vessel wall 52 while the suture needle 50 is pushing against and penetrating the opposite side 55. This causes a rather long segment of the suture needle 50 to be exposed outside of the suture guide 51, which reduces the amount of penetration force that can be applied before the suture needle 50 buckles due to compressive load. The vessel 53 may also deflect into an oval shape, which increases the effective diameter of the vessel 53.

Figure 31:
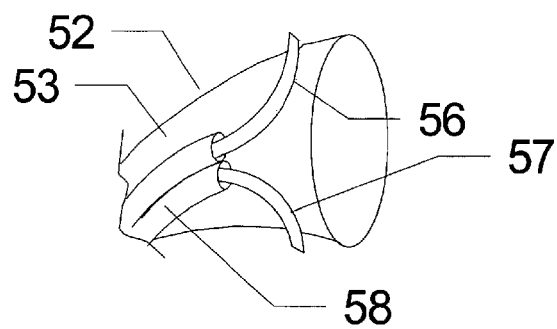
FIG. 31 shows a pair of suture needles being used simultaneously to penetrate opposite sides of a vessel wall.
Figure 32:
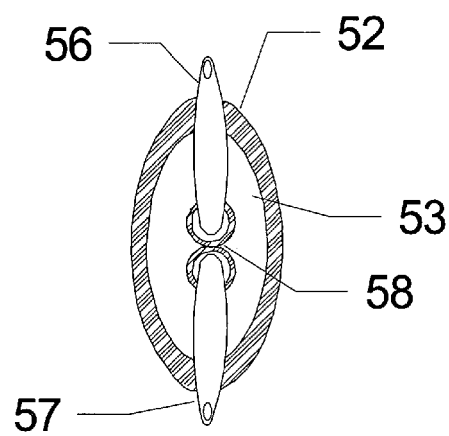
FIG. 32 shows an end view of the assembly shown in FIG. 31.

FIGS. 31 and 32 show a pair of suture needles 56, 57 being used with a multiple lumen suture guide 58 to penetrate a wall of a large vessel 53. By comparing FIGS. 31 and 32 with FIGS. 29 and 30, it can be seen that the use of two suture needles 56, 57 simultaneously may provide a significant advantage over the technique using only a single suture needle 50. By deploying two needles 56, 57 simultaneously, the needles serve to center the multiple lumen suture guide 58 within the vessel 53, effectively reducing the exposed needle length by approximately one half.

Various cinch mechanisms for use in the present invention will now be described with reference to FIGS. 33 to 38 of the drawings.

FIGS. 33 and 34 show two examples of multiple lumen cinch rings that can be used in the present invention. The cinch ring 59 shown in FIG. 33 has two lumens, while the cinch ring 60 shown in FIG. 34 has four lumens. The particular number of lumens for the cinch ring can be selected based on the number of sutures to be installed.

A single lumen cinch ring 61 having a directional biasing structure 62 is shown in FIGS. 35 and 36. The directional biasing structure 62 comprises a plurality of angled elements 63 imbedded in the wall 64 of the cinch ring 61. The angled elements 63 can be wires or other suitable resilient structures. The angled elements 63 are inserted at an angle so that they are deflected slightly as the suture 65 is inserted into the cinch ring 61. The angled elements 63 rest on the suture 65 and allow movement in a direction that deflects the angled elements 63 outwards. However, if the cinch ring 61 is moved in the opposite direction, the angled elements 63 will dig into the suture 65 and prevent its movement.

Cinch rings 66, 67 can also be crimped in place, as shown in FIG. 37, or fused to the sutures, as shown in FIG. 38. The cinch ring 67 can be fused to the sutures by applying heat to the cinch ring via induction, conduction, resistive, or ultrasonic energy application.

Figure 39:
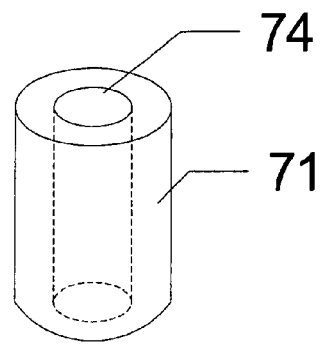
FIGS. 39 to 43a illustrate an expandable anchor device for installing sutures in a percutaneous medical procedure according to the present invention.
Figure 40:
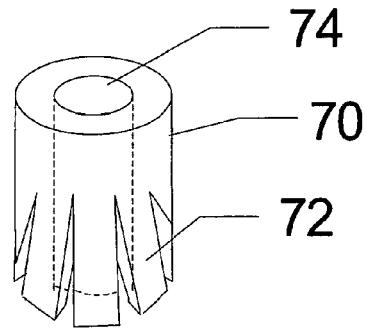
Figure 41:
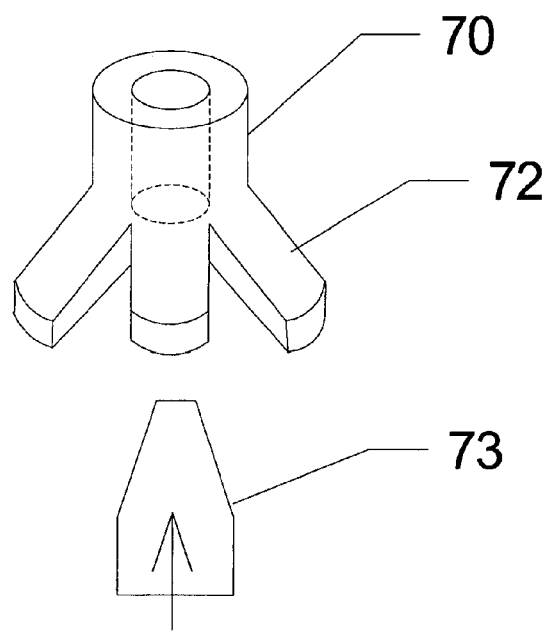

FIGS. 39 to 43a illustrate an expandable anchor device 70 for installing sutures according to the present invention. The anchor device 70 is constructed from a polymeric or metallic tube 71, as depicted in FIG. 39. The tube 71 is counterbored and split at one end to form an expandable portion 72, as shown in FIG. 40. The expandable portion 72 is flared using a heated die 73 or other suitable process, as shown in FIG. 41. The result is an anchor structure having a center lumen 74 and an expanded portion 72 that can be temporarily compressed during deployment.

Figure 42:
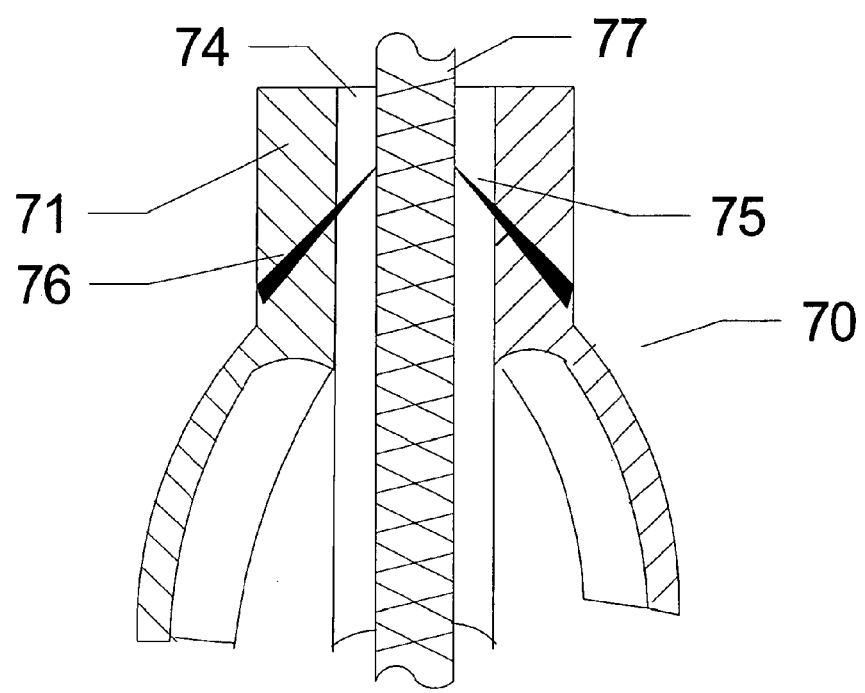

As shown in FIG. 42, a directional biasing structure 75 can be provided within the anchor device 70, similar to the directional biasing structure described above for the cinch rings. The directional biasing structure 75 comprises a plurality of angled elements 76 imbedded in the wall of the tube 71 and extending into the lumen 74. The angled elements 76 can be wires, pins, or other suitable resilient structures. The angled elements 76 are inserted at an angle so that they allow movement in a first direction and resist movement by digging into the suture 77 in a second direction.

Figure 43:
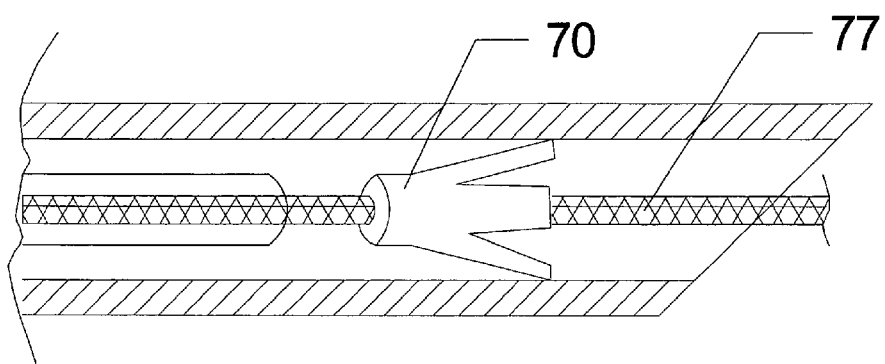
Figure 43A:
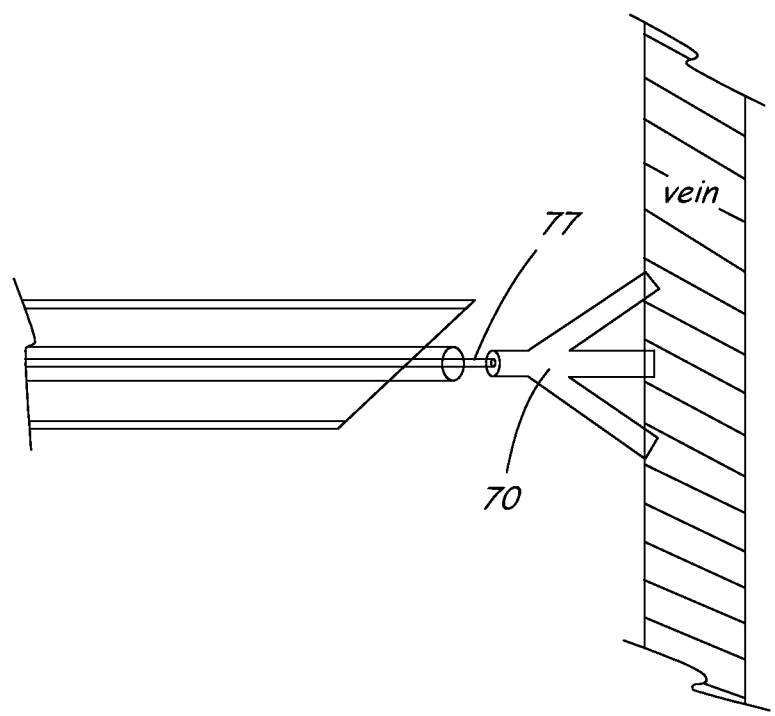

FIG. 43 shows the anchor device 70 contracted within a suture needle 78 for deployment through a vessel wall, while FIG. 43a shows the anchor device 70 in its deployed condition against the vessel wall.

Figure 44:
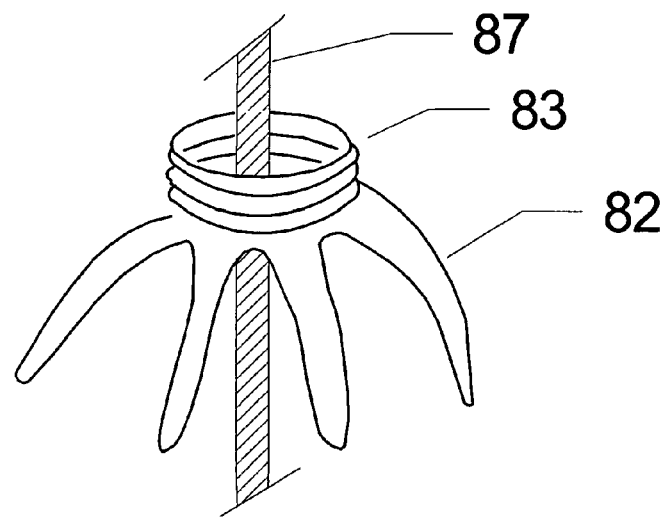
FIGS. 44 to 47 show an expandable suture anchor device for installing sutures in a percutaneous medical procedure according to the present invention.
Figure 45:
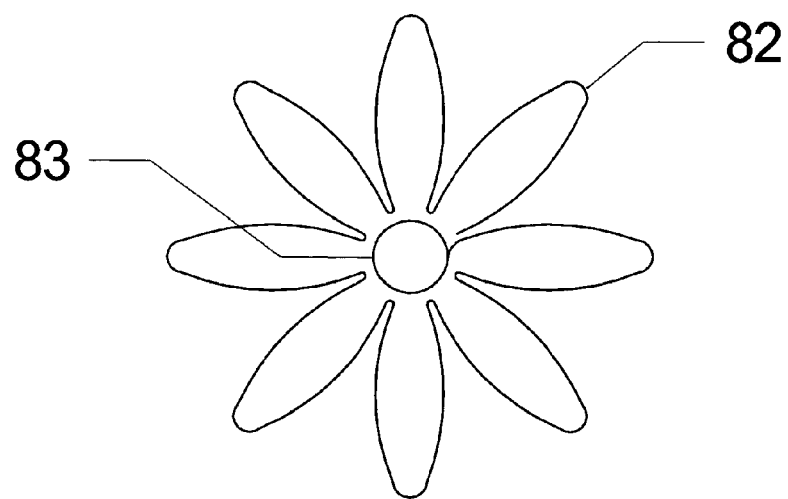
Figure 46:
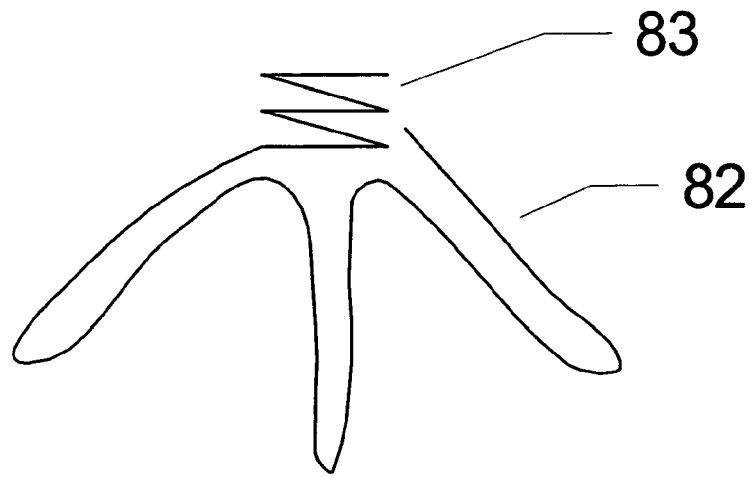
Figure 47:
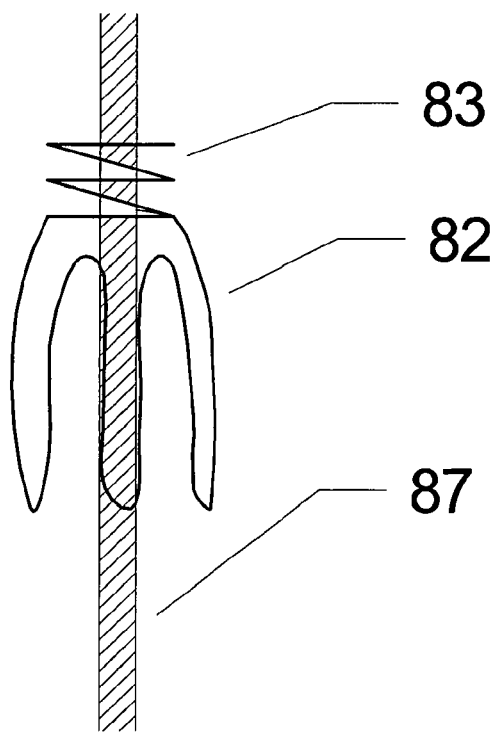

FIGS. 44 to 47 show an expandable suture anchor device 82 for use in the present invention. FIGS. 44, 45 and 46 show the suture anchor device 82 in its expanded condition, while FIG. 47 shows the device 82 in its compressed condition. The suture anchor device 82 is constructed of polymeric or metallic filament that is heat set into its desired shape. The center lumen of the anchor device 82 is formed by a spring structure 83 that can be mechanically expanded to allow the anchor device 82 to be slid over the suture, and then released so that the spring structure 83 squeezes the suture tightly and locks the anchor device 82 in place on the suture.

Figure 48:
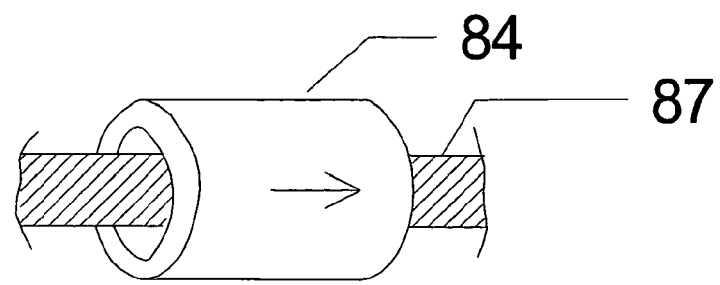
FIG. 48 shows a cinch ring being applied over a single suture.
Figure 49:
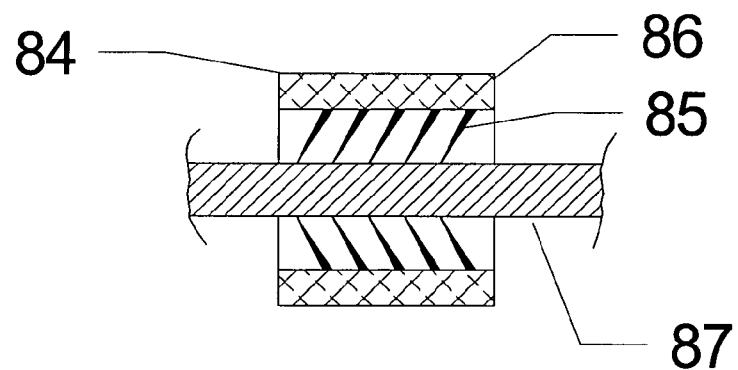
FIG. 49 is a cross sectional side view of the cinch ring of FIG. 48 showing a directional biasing structure extending into a lumen thereof.

FIGS. 48 and 49 show a cinch ring 84 that is directionally biased using wires or other suitable angled elements 85 imbedded in the wall 86 of the cinch ring 84 as shown. The angled elements 85 are inserted so that they are deflected slightly as the suture 87 is inserted into the ring 84. The angled elements 85 rest on the suture 87 and allow movement in a direction that deflects the angled elements 85 outwards. If the ring 84 is moved in the opposite direction, the angled elements 85 will dig into the suture 87 and prevent its movement.

Figure 50:
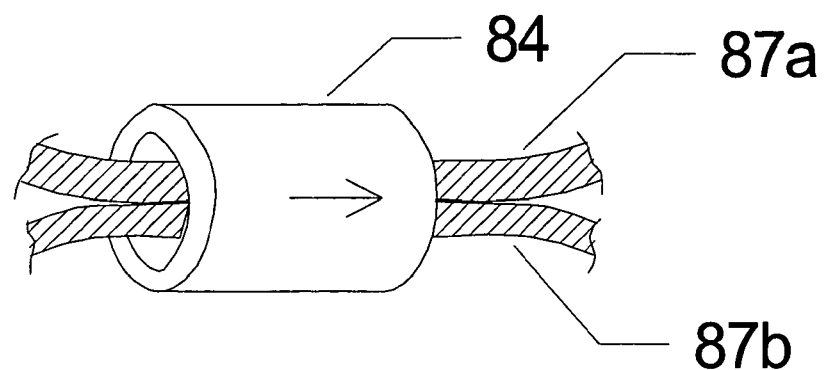
FIG. 50 shows a cinch ring being applied over a plurality of sutures.
Figure 51:
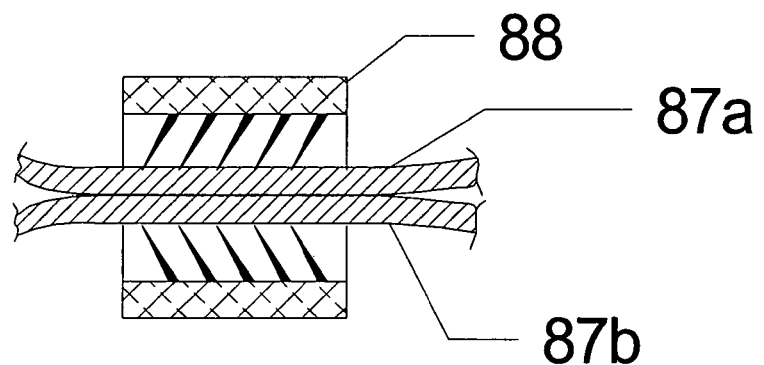
FIG. 51 is a cross sectional side view of the cinch ring of FIG. 50 showing a directional biasing structure extending into a lumen thereof.

FIGS. 50 and 51 show a cinch ring 88 similar to that shown in FIGS. 48 and 49, except that it is sized and constructed to fit over two sutures 87a, 87b instead of one.

Figure 52:
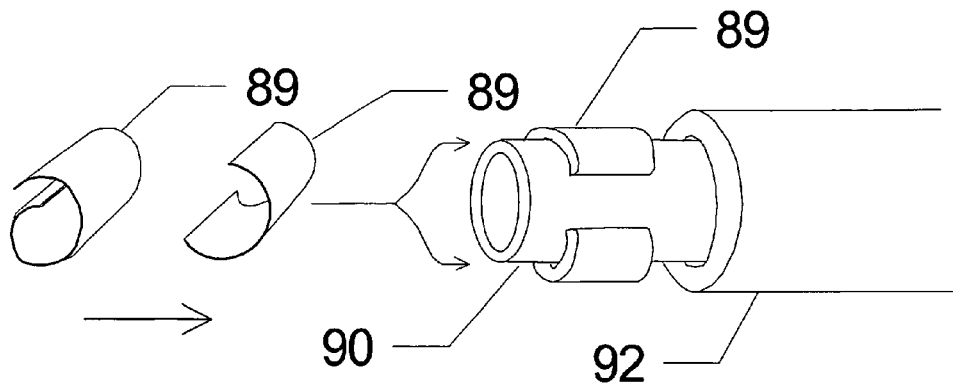
FIG. 52 shows an assembly sequence for preparing a resilient cinch clip to be deployed over a suture.
Figure 53:
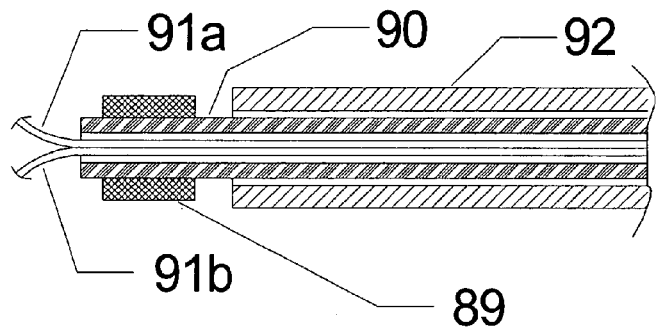
FIG. 53 is a cross section view of the resilient cinch clip just before it is pushed off of the distal end of the suture needle.
Figure 54:
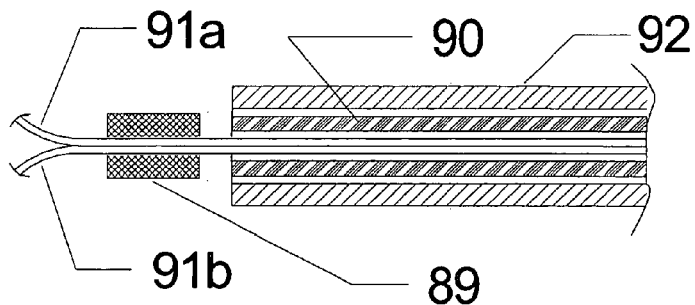
FIG. 54 is a cross section view of the resilient cinch clip just after it is pushed off of the distal end of the suture needle onto the suture.

FIGS. 52 to 54 show the use of a cinch ring comprising a radial spring 89 that can be expanded and placed on a delivery tube 90. This delivery tube 90 is used to cinch the sutures 91a, 91b, and then a push tube 92 is used to slide the radial spring 89 off of the delivery tube 90. As this occurs, the radial spring 89 recovers (compresses) to its original shape and clamps over the sutures 91a, 91b to keep them cinched in place.

Figure 55:
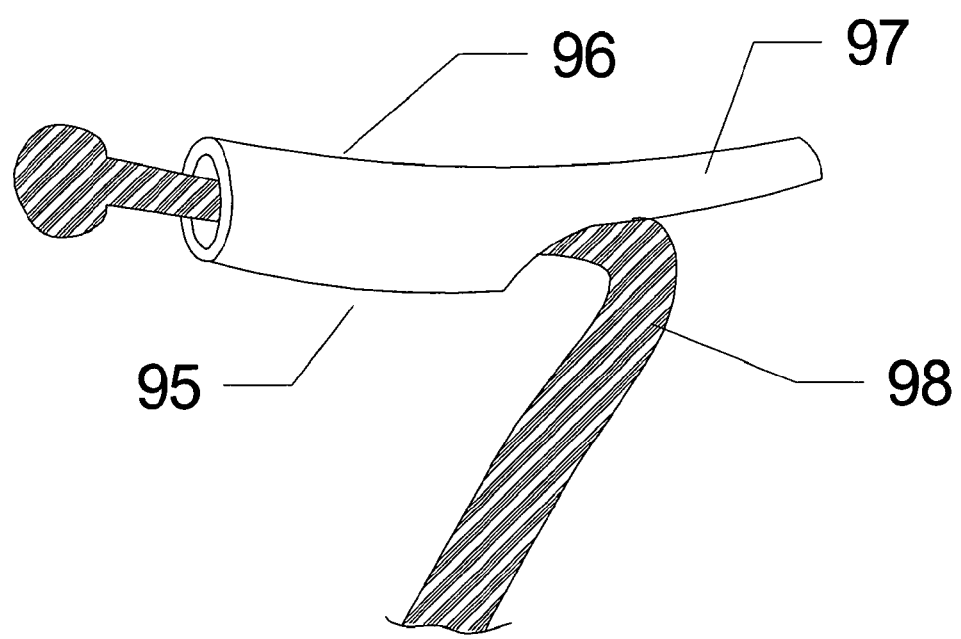
FIG. 55 shows a suture with a low profile, T-bar anchor mechanism.
Figure 57:
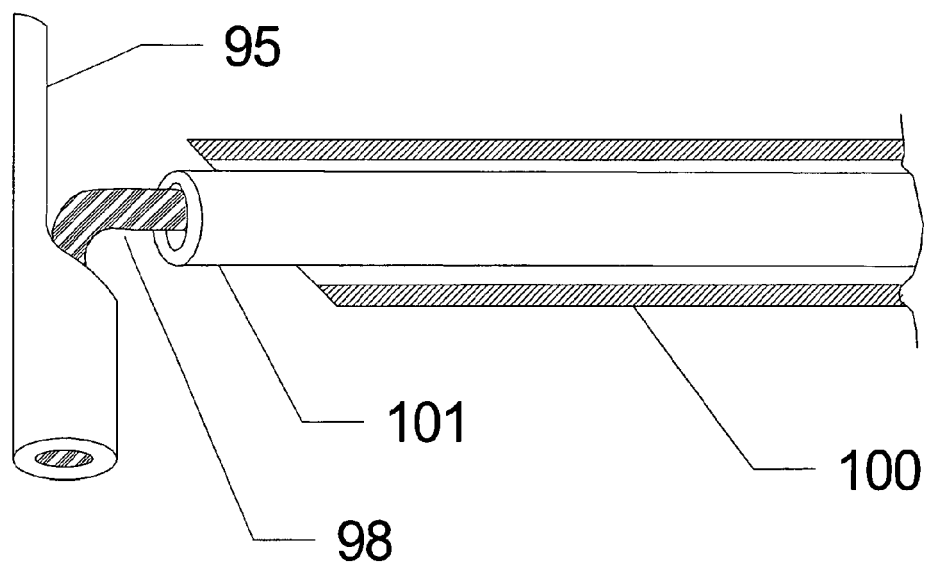
FIG. 57 shows the T-bar anchor mechanism and suture after the anchor mechanism is ejected from the distal tip of the delivery needle for deployment.
Figure 58:
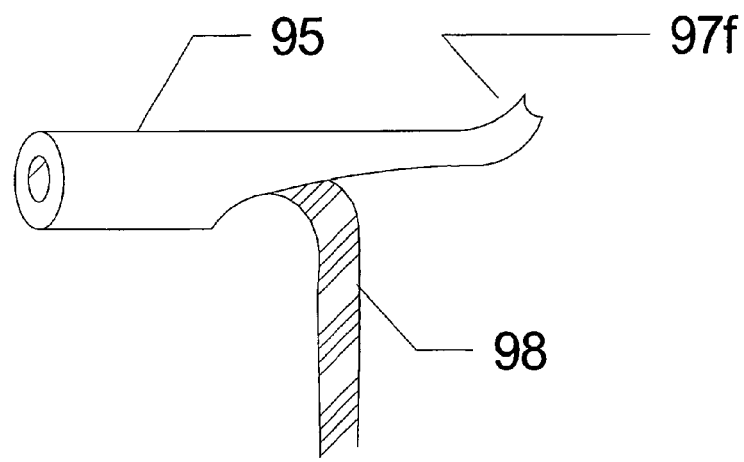
FIG. 58 shows the T-bar anchor mechanism with a flared tip to promote proper deployment.
Figure 59:
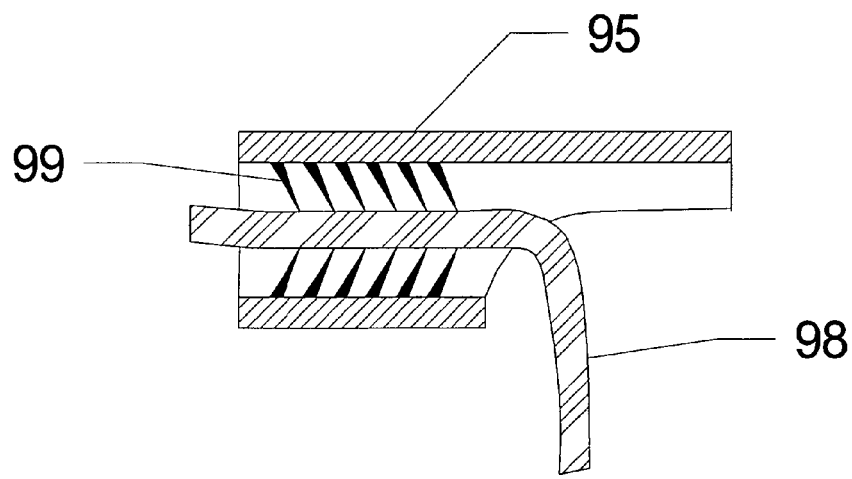
FIG. 59 is a cross sectional view of the T-bar anchor mechanism with a directional biasing structure within the anchor mechanism.

FIGS. 55 to 59 show a low profile, T-bar anchor mechanism 95 that can be used to perform the medical procedure of the present invention. The T-bar anchor mechanism 95 is formed from a polymer or metallic tube 96 that is machined at one end 97 to remove approximately half of the tube wall over half the length of the tube 96, as shown in FIG. 55. A suture 98 is inserted into the tube 96 as shown. The anchor mechanism 95 can be allowed to slide freely over the suture 98, or a knot can be provided in the suture 98 to keep the anchor mechanism 95 from sliding past a certain point (e.g., the distal end). Alternatively, a directional biasing structure 99 can be provided within the anchor mechanism 95, as shown in FIG. 59.

Figure 56:
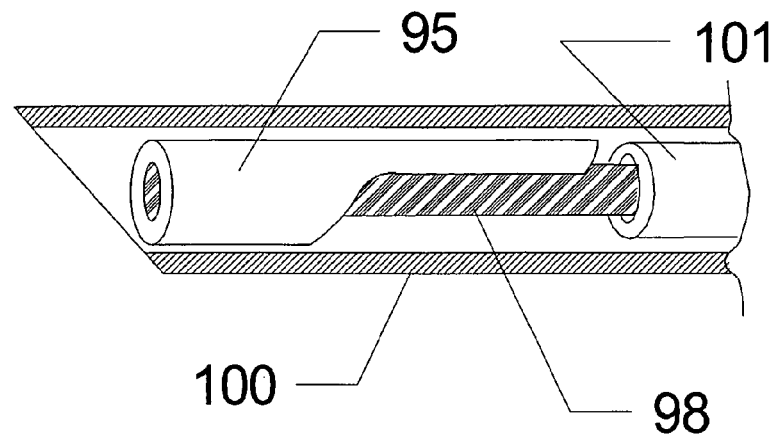
FIG. 56 shows the T-bar anchor mechanism and suture inserted into a delivery needle with a push tube for advancing the anchor mechanism through the delivery needle.

FIG. 56 shows the T-bar anchor mechanism 95 and suture 98 inserted into a delivery needle 100 with a push tube 101 for advancing the anchor mechanism 95 through the delivery needle 100. The cut away portion of the tube wall allows the anchor mechanism 95 to be inserted in line with the suture 98 and have a minimal profile within the delivery needle 100. Upon ejection out of the distal tip of the delivery needle 100, the T-bar anchor mechanism 95 will deploy as shown in FIG. 57. This will allow the suture 98 to be anchored to the vessel wall in a manner similar to the expanding anchors described above.

FIG. 58 shows the T-bar anchor mechanism 95 with a flared tip 97f to promote proper deployment. Various shapes and sizes of the T-bar anchor mechanism can be developed by those skilled in the art to optimize its performance in the medical procedures described herein.

Figure 60:
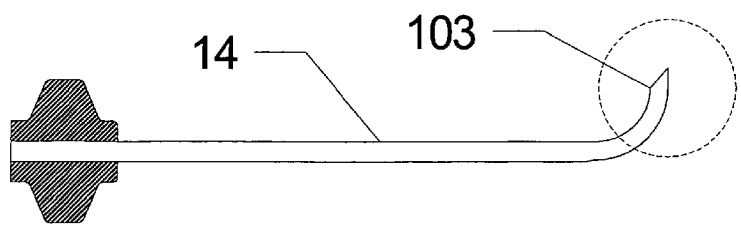
FIGS. 60 to 65 illustrate various embodiments of a suture needle having a stylet for penetrating the vessel wall.

FIGS. 60 to 65 illustrate various ways that a stylet 102 can be used with the suture needle 14 of the present invention to help penetrate a vessel wall. FIG. 60 shows a suture needle 14 with a distal tip 103, while FIGS. 61 to 65 provide detail cross sections of various suture needle distal tips.

Figure 61:
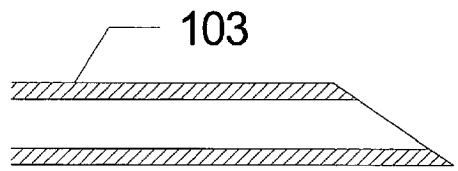
Figure 62:
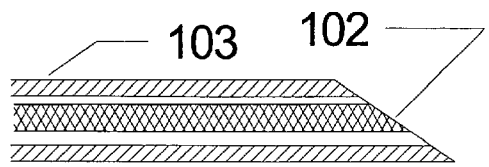
Figure 63:
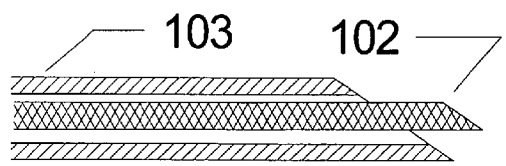

FIG. 61 shows an angled suture needle distal tip 103 without a stylet. FIG. 62 shows the suture needle distal tip 103 with a stylet 102 that does not exit the needle. FIG. 63 shows the suture needle distal tip 103 with a stylet 102 that is exposed and used to pre-penetrate the vessel wall.

Figure 64:
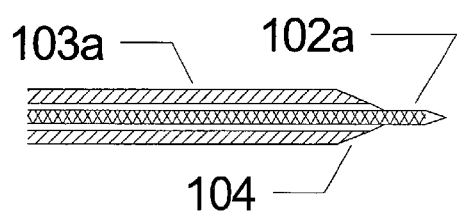
Figure 65:
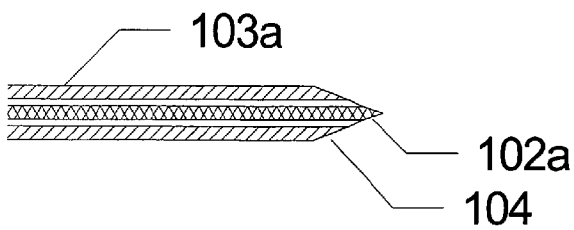
Figure 66:
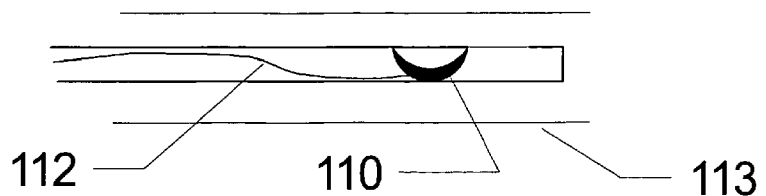
FIGS. 66 to 69 show a series of steps for performing a percutaneous medical procedure for closing a vessel by installing a combination of clips and sutures.
Figure 67:
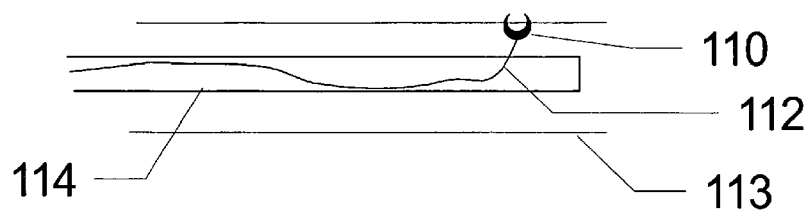

FIGS. 64 and 65 show suture needle distal tips 103a with conical cuts 104 and stylets 102a that are matched to the conical cuts 104. The stylets 102a can be used to pre-penetrate or puncture the vessel wall, and then can be retracted or removed from the suture needle 14 to avoid over-penentration. The conical cut suture needle 14 can then be used to push into the surrounding tissue without penetrating it. The conical cut suture needle 14 can be used to aid in adding fluidic media 22 around the vessel.

FIGS. 66 to 69 show an embodiment of the present invention in which resilient clips 110, 111 and sutures 112 can be combined in a procedure for closing a vessel 113. In this embodiment, a first resilient clip 110 is inserted to the treatment location in the vessel 113 using a deployment catheter 114 and placed against the vessel wall. The first clip 110 is attached to the distal end of a suture 112. The first clip 110 is deployed in such a way that it moves from an expanded position during insertion into a contracted position for gripping or clamping to the vessel wall (i.e., without using a suture needle to penetrate the wall). The first clip 110 is thus anchored to the vessel wall to function in generally the same manner as the expanding anchors described above.

Figure 68:
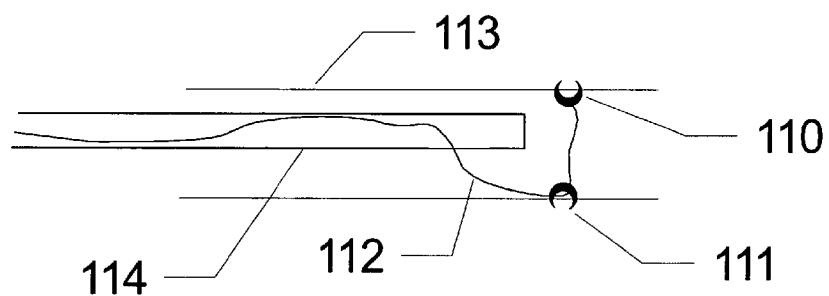
Figure 69:
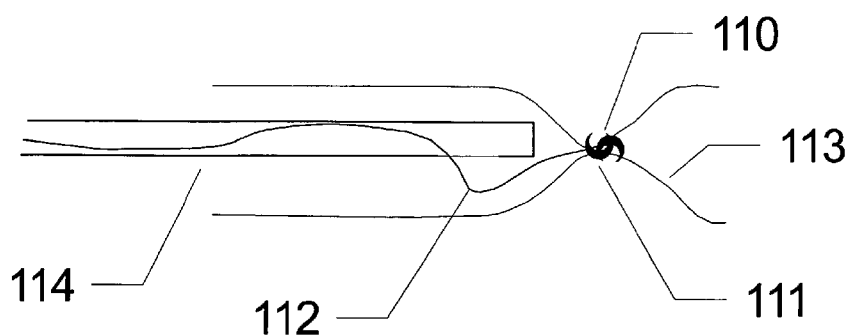

A second sliding clip 111 is then slid over the suture 112 and pushed to the distal end of the deployment catheter 114. The second clip 111 is placed against an opposite side of the vessel wall from the first clip. The second clip 111 is deployed similar to the first clip 110 so that it grips or clamps to the vessel wall. After the second clip 111 is anchored to the vessel wall, the suture 112 is pulled to cinch the vessel closed, as shown in FIGS. 68 and 69. A cinch ring or other suitable mechanism can then be installed over the suture to maintain the closed condition of the vessel 113.

The resilient clips shown in FIGS. 66 to 69 could also be used with multiple sutures in a procedure to close a vessel. In this case, the second clip would be attached to a distal end of a second suture, and the procedure would be similar to the procedure described above (e.g., FIGS. 15 to 22) for installing multiple sutures with fixed anchors at their ends.

Figure 70:
FIG. 70 shows a suture that can be used in a percutaneous medical procedure to close a vessel.

FIG. 70 shows a suture 115 for use in a percutaneous medical procedure to close a vessel. It is contemplated that the suture 115 can be installed using the suture needles and other instruments described herein to close a vessel without using an anchor or a cinch mechanism. However, the use of anchors and cinch mechanisms in the present invention as described above should provide a superior medical procedure.

Figure 71:
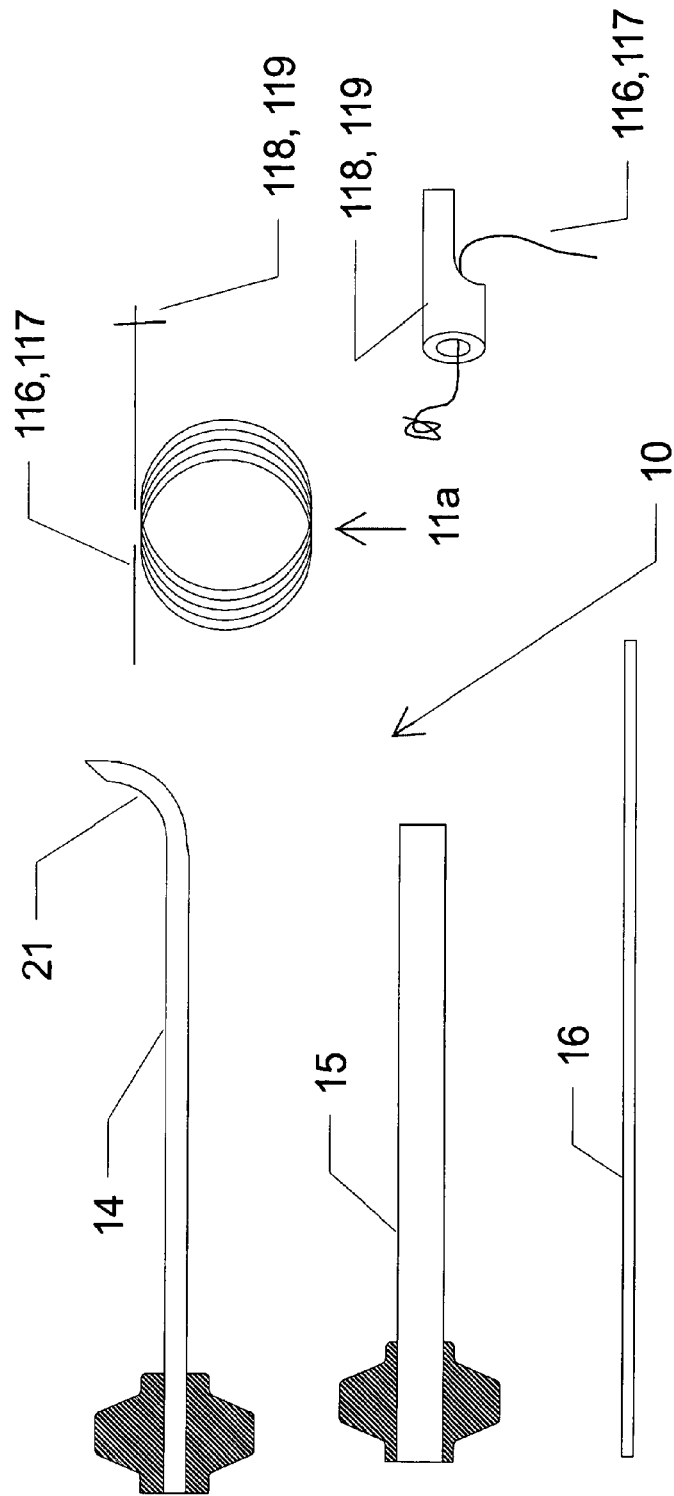
FIG. 71 shows the various components of an endovascular instrument and device for installing sutures with T-bar anchor mechanisms in a percutaneous medical procedure according to the present invention.

FIGS. 71 to 82 illustrate another embodiment of the present invention in which an endovascular instrument 10 is used to install sutures 116, 117 with T-bar anchor mechanisms 118, 119 for closing a vessel 13. The various components of the endovascular instrument 10 and T-bar anchor mechanisms 118, 119 are shown in FIG. 71. The instrument 10 includes a suture needle 14, a suture guide 15, and a suture push tube 16. The mechanical closure 11a includes a first suture 116 with a first T-bar anchor mechanism 118 fixed at its distal end, a second suture 117 with a second T-bar anchor mechanism 119 fixed at its distal end, and a cinch ring 120. The details of the T-bar anchor mechanisms 118, 119 are shown in FIG. 71a. A knot 121 is provided at the distal end of the sutures 116, 117 to keep the anchor mechanisms 118, 119 from sliding off of the distal end of the sutures 116, 117.

Figure 72:
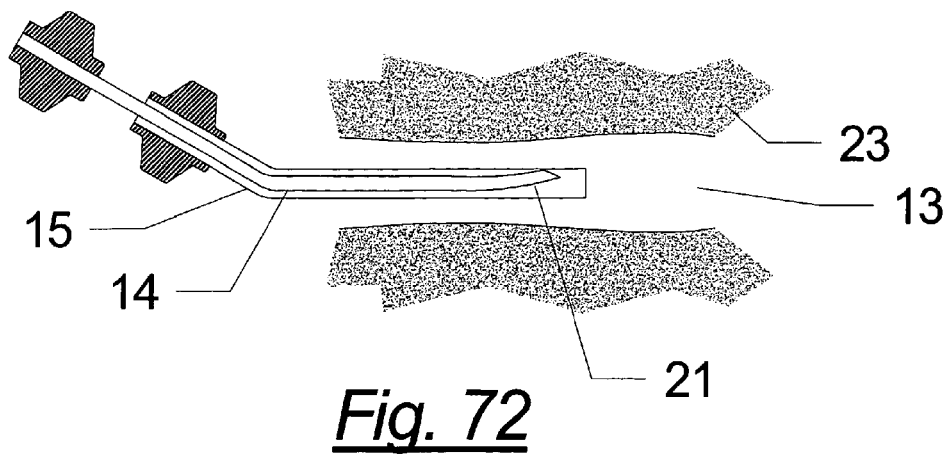
FIGS. 72 to 82 show a series of steps for performing a percutaneous medical procedure for closing a vessel using the instrument shown in FIG. 71 to install multiple sutures with T-bar anchor mechanisms.
Figure 73:
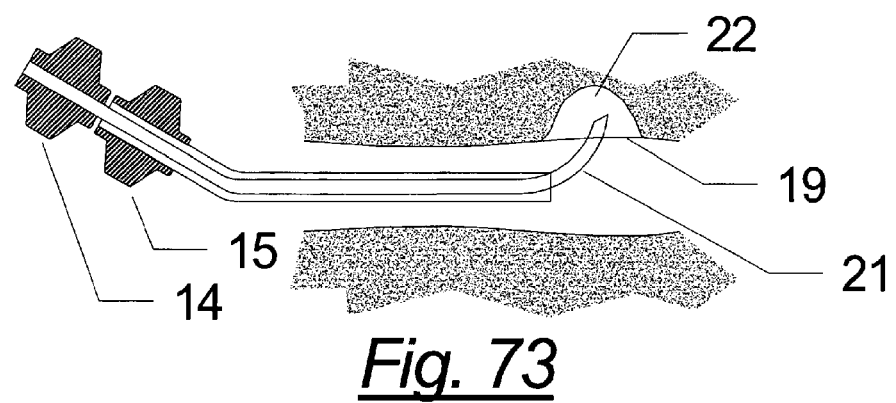

FIGS. 72 to 82 show a series of steps for performing the medical procedure using the instrument 10 and the mechanical closure 11a shown in FIG. 71 to close the vessel 13. The suture needle 14 is inserted into the suture guide 15 so that the preset curve in the distal portion 21 of the suture needle 14 is straightened within the suture guide 15. The assembly of the suture guide 15 and the suture needle 14 is then inserted into the vessel 13 to a desired treatment location (closure point), as shown in FIG. 72. The suture needle 14 is then advanced within the suture guide 15 until the distal portion 21 of the suture needle 14 exits the suture guide 15, and the preset curve in the distal portion 21 causes the suture needle 14 to curve toward and penetrate the vessel wall 19 at a first location, as shown in FIG. 73.

A fluidic media 22, such as saline, is injected through the suture needle 14 after the needle 14 penetrates through the vessel wall 19. The fluidic media 22 surrounds the vessel 13 and isolates the vessel wall 19 from surrounding tissue 23. The fluidic media 22 also imparts a closing pressure on the vessel 13, which can facilitate the closing procedure. The fluidic media 22 can also be injected externally using a conventional needle and syringe, and can be injected prior to the suture needle 14 penetrating the vessel wall 19.

Figure 74:
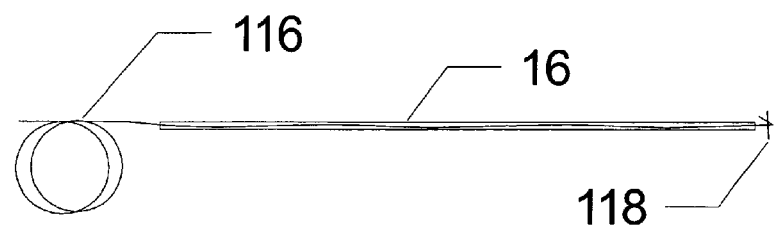
Figure 75:
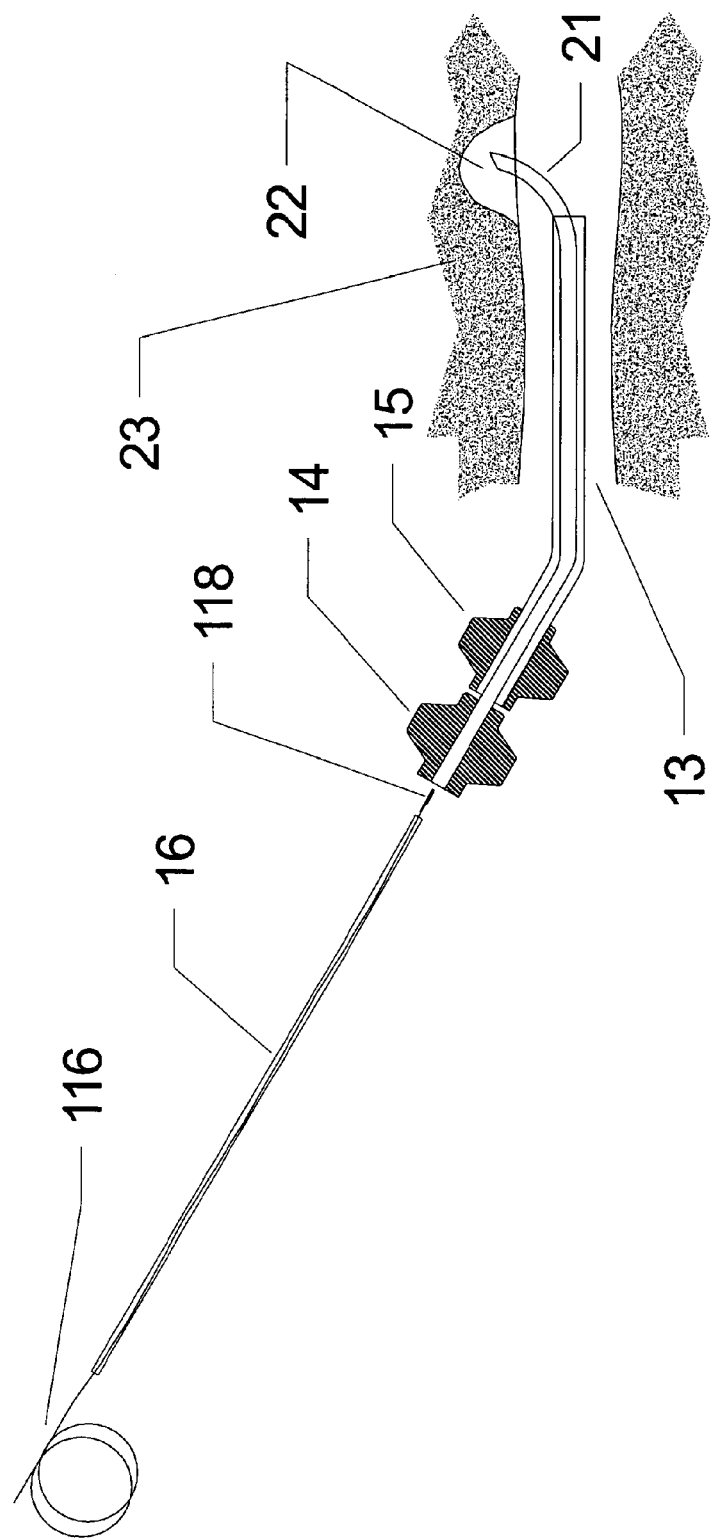
Figure 76:
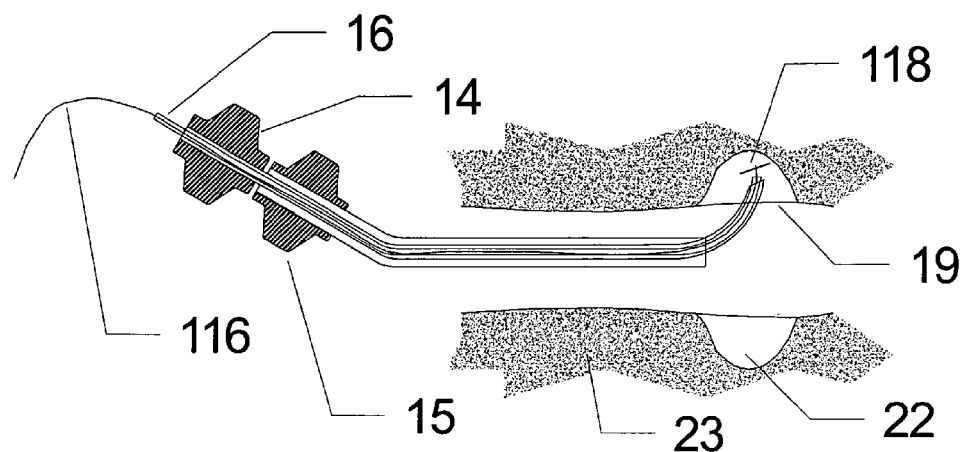

The first suture 116 with the first T-bar anchor 118 fixed at its distal end is then loaded into the suture push tube 16, as shown in FIG. 74. The push tube 16 with the first suture 116 and the first T-bar anchor 118 are then inserted into the lumen of the suture needle 14 with the T-bar anchor 118 folded in line with the suture 116, as shown in FIG. 75. The push tube 16 is advanced through the suture needle 14, along with the first suture 116 and first T-bar anchor 118, until the first suture 116 and first T-bar anchor 118 exit the distal end of the suture needle 14 into the fluidic media 22 surrounding the vessel 13, as shown in FIG. 76. The first T-bar anchor 118 deploys into its T-configuration relative to the suture 116 upon exiting the suture needle 14.

Figure 77:
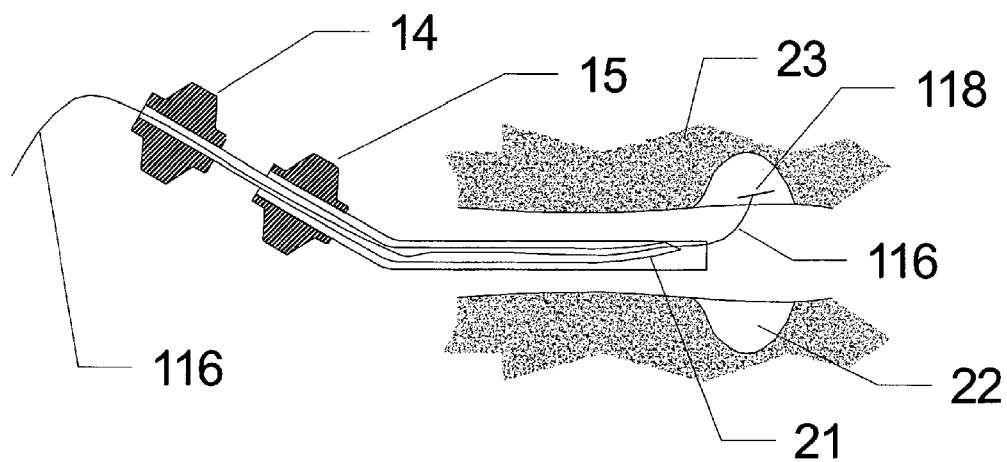

The push tube 16 is then removed and the suture needle 14 is retracted back into the suture guide 15 leaving the first suture 116 and the first T-bar anchor 118 anchored in the vessel wall 19, as shown in FIG. 77. The suture needle 14 is then removed from the suture guide 15, slid off of the first suture 116, and reinserted back into the suture guide 15. Before advancing the suture needle 14 out of the distal end of the suture guide 15, the suture needle 14 is rotated about its longitudinal axis (e.g., 180 degrees). The suture needle 14 is then advanced within the suture guide 15 until the distal portion 21 of the suture needle 14 exits the suture guide 15 and curves toward the vessel wall 19. The suture needle 14 continues to be advanced until its distal tip penetrates the vessel wall 19 at a second location angularly spaced from the first location.

Figure 78:
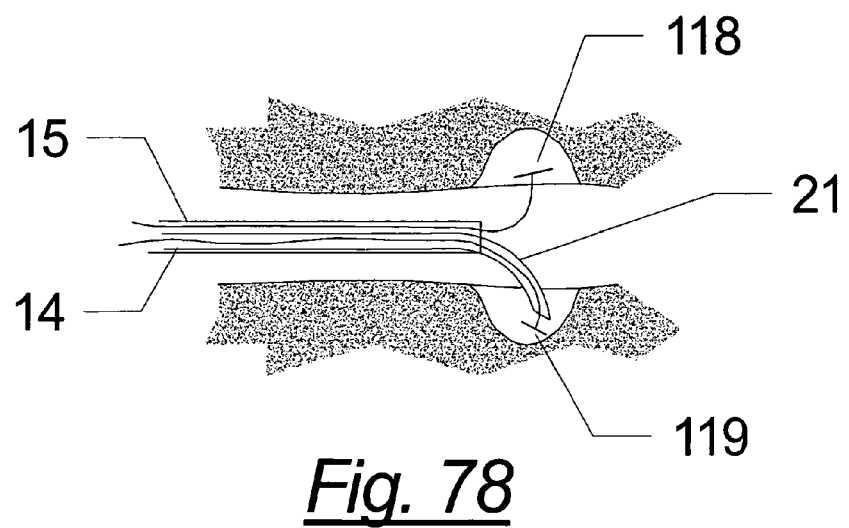

A second suture 117 with a second T-bar anchor 119 fixed at its distal end is then loaded into the suture push tube 16 and inserted into the lumen of the suture needle 14. The second suture 117 and second T-bar anchor 119 are advanced through the suture needle 14 until the second T-bar anchor 119 exits the distal end of the suture needle 14 into the fluidic media 22 surrounding the vessel 13, as shown in FIG. 78. The second T-bar anchor 119 adopts its T-shaped configuration outside the vessel wall 19 upon exiting the suture needle 14.

Figure 79:
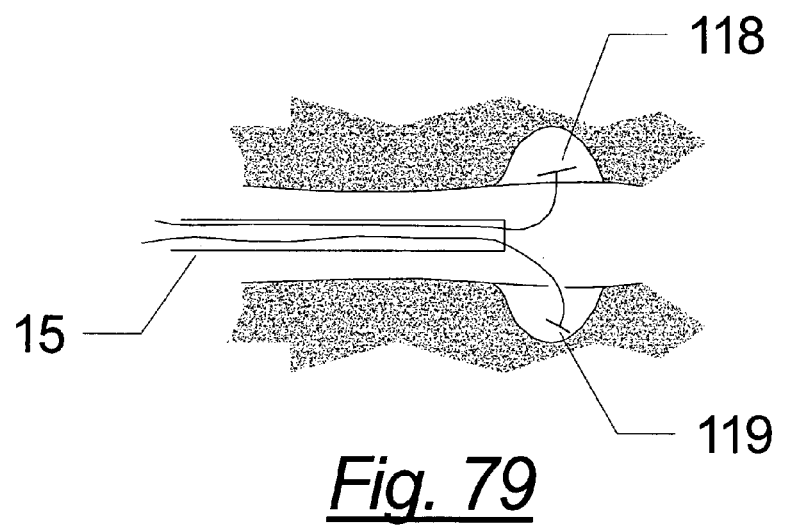

The push tube 16 and suture needle 14 are then retracted and removed from the suture guide 15 leaving the second suture 117 and the second T-bar anchor 119 anchored in the vessel wall 19, as shown in FIG. 79. These steps can be repeated, if desired, to install additional sutures with expanding anchors fixed at their distal ends.

Figure 80:
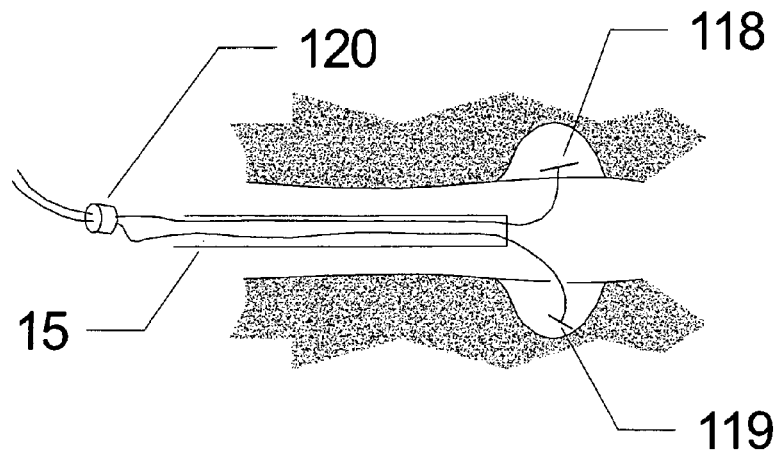
Figure 81:
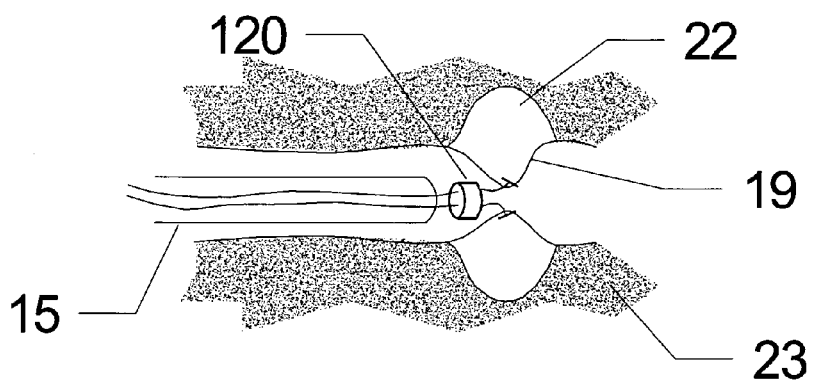
Figure 82:
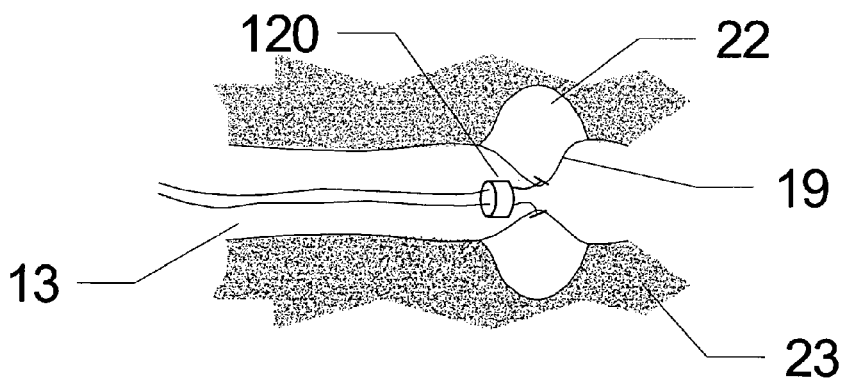
Figure 83:
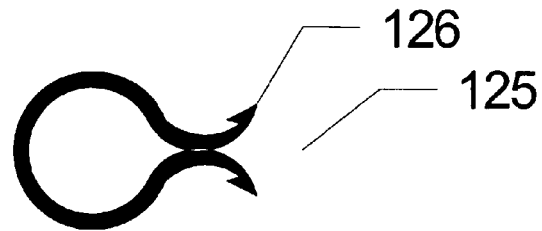
FIG. 83 shows a horseshoe-shaped clip having barbs or T-bars at its ends for use as a mechanical closure to clip a vessel shut.
Figure 84:
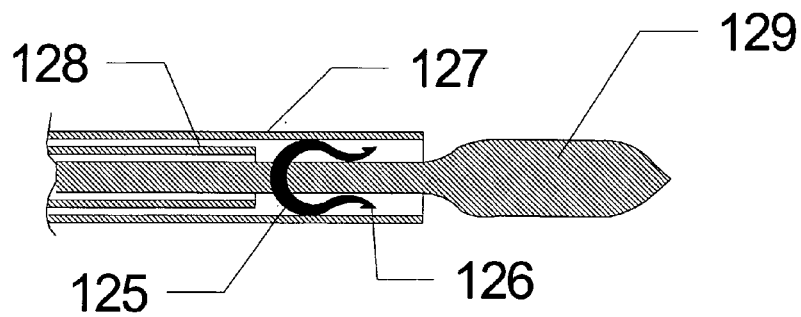
FIG. 84 shows a guide catheter with a pusher and expander catheter for installing the clip shown in FIG. 83.
Figure 85:
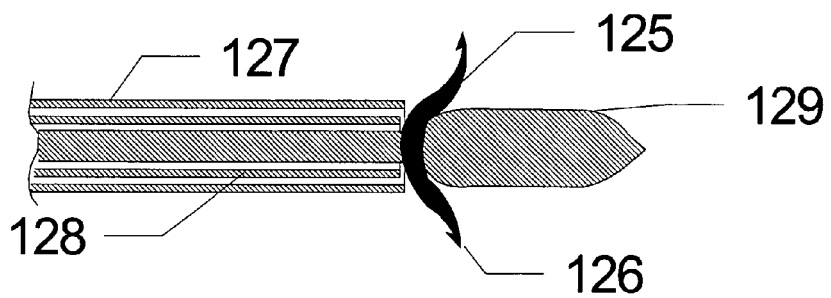
FIG. 85 shows the expander catheter being used to deflect the legs of the clip outward to penetrate the vessel wall.
Figure 86:
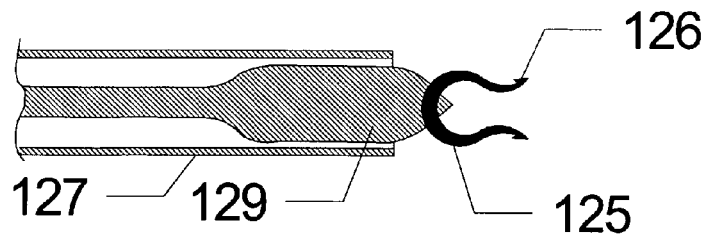
FIG. 86 shows the legs of the clip being retracted to their original position after the expander catheter is retracted from the clip.
Figure 87:
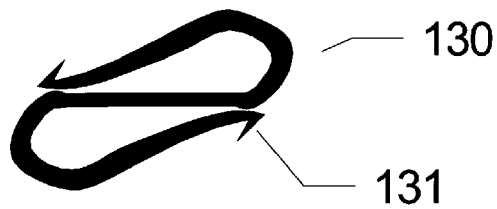
FIG. 87 shows an S-shaped clip having barbs or T-bars at its ends for use as a mechanical closure to clip a vessel shut.
Figure 88:
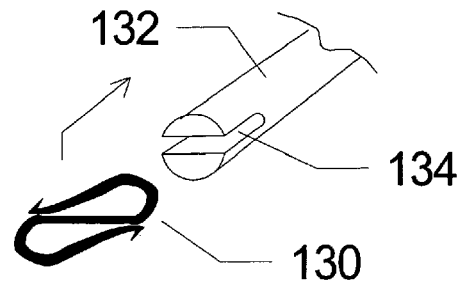
FIG. 88 shows a torque tube for use in deploying the S-shaped clip of FIG. 87.
Figure 90:
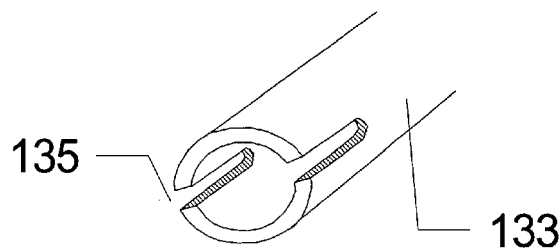
FIG. 90 shows an outer guide tube which is used in conjunction with the torque tube to deploy the S-shaped clip.

A cinch ring 120 is then slid over the first and second sutures 116, 117 (and the additional sutures, if any) and pushed through the suture guide 15 and into position using a push tube 16, as shown in FIG. 80. The cinch ring 120 is used in conjunction with the sutures 116, 117 to pull the vessel 13 closed and keep it closed, as shown in FIG. 81. The suture guide 15 can then be removed to complete the procedure, as shown in FIG. 82.

FIGS. 83 to 86 show another embodiment of the present invention in which a horseshoe-shaped clip 125 having barbs or T-bars at its ends 126 is used as a mechanical closure to clip a vessel shut. The clip 125 can be installed by loading it into a guide catheter 127 along with a pusher 128 and an expander catheter 129. Once in the desired position, the clip 125 is ejected out of the guide catheter 127 with the pusher 128. The clip 125 will then ride up on the expander catheter 129 causing its legs to be deflected outward to penetrate the vessel wall. The barbs or T-bars at the ends 126 of the legs of the clip 125 serve to anchor the legs in the vessel wall upon penetration. The pusher 128 and expander catheter 129 are then retracted leaving the clip 125 to contract and close the vessel.

FIGS. 87 to 93 show another embodiment of the present invention in which a generally S-shaped clip 130 with barbs or T-bars at its ends 131 is used as a mechanical closure to close a vessel. The S-shaped clip 130 is applied radially relative to the direction of flow in the vessel. The S-shaped clip 130 is deployed within the vessel by using an inner torque tube 132 (see FIG. 88) and an outer guide tube 133 (see FIG. 90) to expand the clip 130 until the pointed ends 131 penetrate a wall of the vessel.

Figure 89:
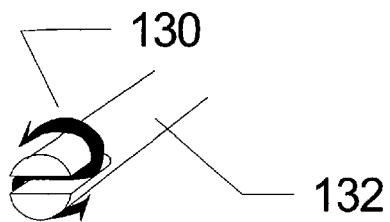
FIG. 89 shows the S-shaped clip loaded into a groove in the end of the torque tube.
Figure 91:
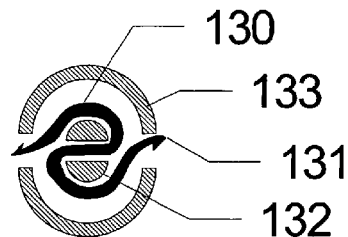
FIG. 91 is an end view of the torque tube and external guide tube showing the S-shaped clip in a position ready to be deployed.
Figure 92:
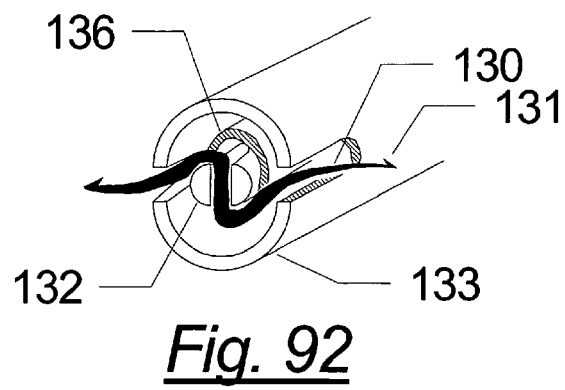
FIG. 92 is an end view of the torque tube and external guide tube showing the S-shaped clip in an expanded condition in which the ends of the clip pierce the vessel walls.
Figure 93:
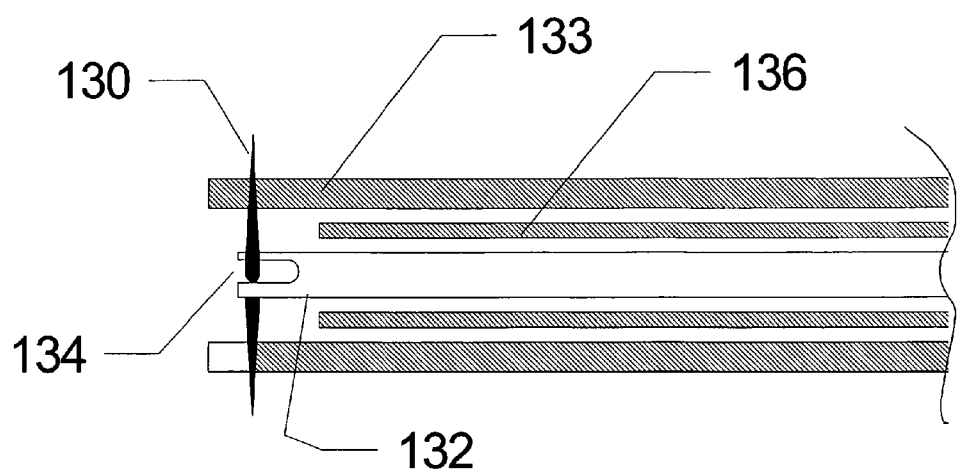
FIG. 93 is a cross section side view of the assembly shown in FIG. 92.
Figure 94:
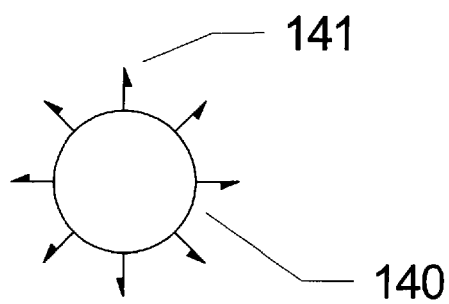
FIG. 94 is an end view of a self-contracting stent with barbs attached to its outer surface for penetrating a vessel wall.

For deployment, the S-shaped clip 130 is loaded into a groove 134 in the end of the torque tube 132, as shown in FIG. 89. The inner torque tube 132 with the S-shaped clip 130 loaded therein is then placed in the outer guide tube 133, with the ends 131 of the S-shaped clip 130 fit within the slots 135 at the end of the outer guide tube 133, as shown in FIG. 91. The inner torque tube 132 is then rotated relative to the outer guide tube 133, causing the S-shaped clip 130 to unwind so that the ends 131 of the S-shaped clip 130 protrude outwardly from the slots 135 in the outer guide tube 133. As the pointed ends 131 of the S-shaped clip 130 protrude outwardly, they penetrate the vessel wall. The barbs or T-bars at the ends 131 of the S-shaped clip serve to anchor the ends 131 in the vessel wall. The torque on the inner torque tube 132 and outer guide tube 133 is then relaxed so that the S-shaped clip 130 returns to its original condition, which contracts and closes the vessel. A pusher tube 136 (see FIG. 93) is inserted between the inner torque tube 132 and the outer guide tube 133 for pushing the S-shaped clip 130 out of the groove 134 of the inner torque tube and the slots 135 of the outer guide tube 133 to complete the deployment.

Another embodiment of the present invention will now be described with reference to FIGS. 94 to 99 of the drawings. In this embodiment, a self-contracting stent 140 with barbs 141 protruding from its outer surface is used to close a vessel 142. The stent 140 is loaded onto a balloon 143, which is inflatable in a conventional manner to enlarge the stent 140 upon deployment.

The stent 140 can be similar to conventional stents used in coronary applications, except that conventional stents are somewhat malleable so that as a balloon is inflated to expand them, they deform and stay in the open or expanded shape to hold the vessel open. In the present embodiment, the stent 140 is constructed out of a resilient material, such as polymer, spring steel, nitenol, or the like, so that the stent 140 will return to its original, contracted condition after the balloon 143 is deflated.

Figure 95:
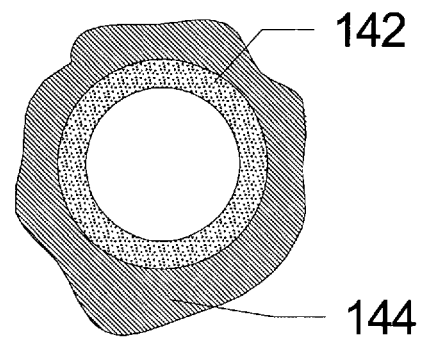
FIG. 95 is a cross section end view of a vessel to be treated with the self-contracting stent shown in FIG. 94.
Figure 96:
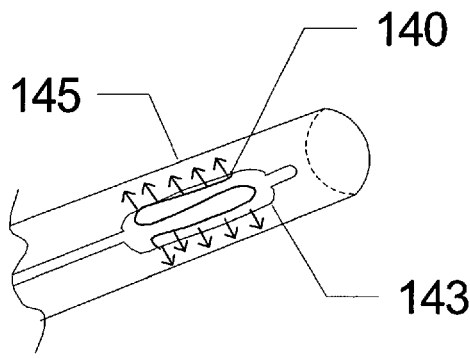
FIG. 96 shows the self-contracting stent loaded onto a balloon with a protective sleeve placed over the stent for insertion into a vessel.
Figure 97:
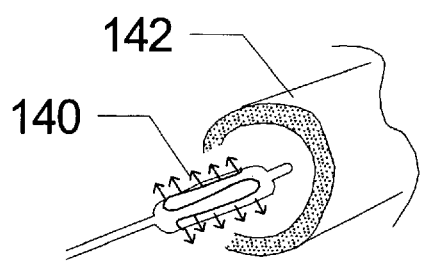
FIG. 97 shows the self-contracting stent deployed at a treatment location within a vessel.

The procedure for closing a vessel 142 using the self-contracting stent 140 starts with injecting fluid 144 around the vessel 142, as shown in FIG. 95, similar to the other embodiments described above. The self-contracting stent 140 is inserted to the treatment location using a protective sleeve 145 that covers the outer surface of the stent 140, as shown in FIGS. 96 and 97. At the treatment location, the protective sleeve 145 is pulled back to cause the stent 140 with the protruding barbs 141 to be exposed.

Figure 98:
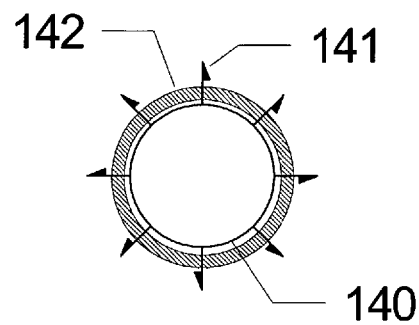
FIG. 98 shows the stent in an expanded condition upon inflation of the balloon with the barbs on the outer surface of the stent penetrating the vessel wall.
Figure 99:
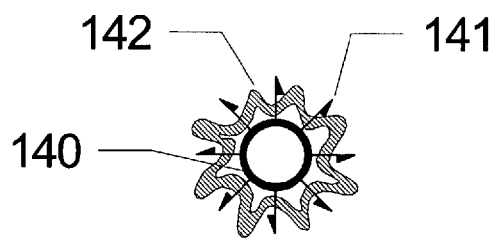
FIG. 99 shows the stent in a contracted condition upon deflation of the balloon, causing the vessel to be closed.
Figure 100:
FIG. 100 is a perspective view of a barbed stent according to another embodiment of the invention.
Figure 101:
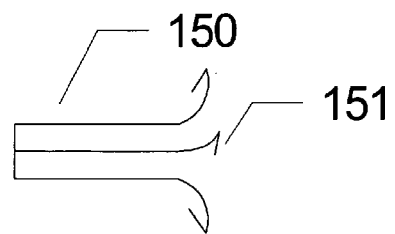
FIG. 101 is a side view of the barbed stent shown in FIG. 100, in a normal contracted condition.

The balloon 143 is then inflated to expand the stent 140, as shown in FIG. 98. As the stent 140 expands, the barbs 141 protruding from the outer surface of the stent 140 are pushed through the vessel wall and become anchored in the vessel wall. The balloon 143 within the stent 140 is then deflated, and the stent 140 springs back to its small, contracted state. As the stent 140 contracts, it pulls the vessel 142 closed, as shown in FIG. 99.

Another embodiment of the present invention will now be described with reference to FIGS. 100 to 104 of the drawings. In this embodiment, another form of a self-contracting stent 150 with barbs 151 protruding outwardly is used to close a vessel.

Figure 102:
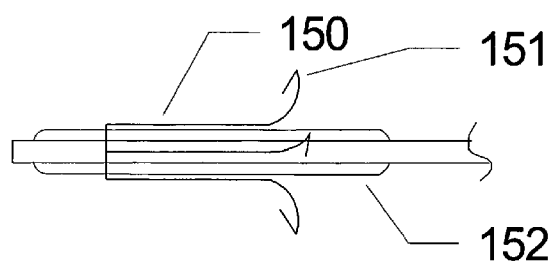
FIG. 102 shows the barbed stent of FIG. 100 loaded onto an uninflated balloon.
Figure 103:
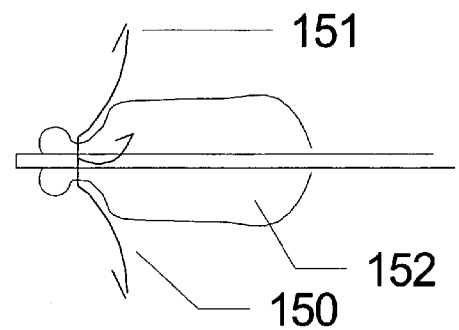
FIG. 103 shows the barbed stent of FIG. 100 in an expanded condition upon inflation of the balloon.

The self-contracting stent 150 can be loaded onto a balloon 152 for expansion at the treatment location, as indicated in FIGS. 102 and 103. Alternatively, the self-contracting stent 150 can be expanded at the treatment location using a mechanical expander 153 that can be pushed or pulled into engagement with the stent 150, as shown in FIG. 104.

As in the embodiment described above, the self-contracting stent 150 can be deployed by inserting the stent 150 to the treatment location using a protective sleeve (not shown), pulling back the protective sleeve to expose the stent 150 with the protruding barbs 151, inflating the balloon 152 to expand the stent 150 and to push the barbs 151 through the vessel wall, and deflating the balloon 152 to cause the stent 150 to spring back to its contracted state and pull the vessel closed. If a mechanical expander 153 is used instead of a balloon 152, the procedure will be adjusted accordingly.

The self-contracting stents 140, 150 shown in FIGS. 94 to 104 can also incorporate a mesh or sock on the stent to assist in clotting when the stents are being used to close a vein.

The endovascular instruments and procedures described herein will allow a safer and more rapid closure of veins than existing procedures. With experience, it is contemplated that the use of these instruments and procedures will expand. For example, these instruments and procedures can be used to treat arterial related diseases, such as arterial hemmorhage or arterial venous malformations. With advancement of the technique, the instruments and procedures could also be used for closing arteries in the trauma setting, closing bleeding gastrointestinal arteries, or closing renal artery aneurysms and arterial venous malformations.

The instruments and procedures described herein will also be useful in transvaginal tubal ligation, and could negate the need for surgery. It is expected that the indications will continue to expand with the use of these instruments and procedures.

While the invention has been specifically described in connection with specific embodiments thereof, it is to be understood that this is by way of illustration and not of limitation, and the scope of the appended claims should be construed as broadly as the prior art will permit.

What is claimed is:

1. A percutaneous medical procedure, comprising:
   inserting an endovascular instrument into a tubular vessel, said instrument comprising an inner torque tube and an outer guide tube having a pair of slots in a distal end thereof; and
   using said instrument to install a mechanical closure for closing the vessel;
   wherein said mechanical closure comprises a clip;
   wherein said clip has an S-shape configuration with pointed ends, and wherein said clip is installed by rotating said inner torque tube relative to said outer guide tube to expand the clip radially outwardly until the pointed ends protrude outwardly from the slots and penetrate a wall of the vessel, and then allowing the clip to contract and close the vessel.

2. A percutaneous medical procedure, comprising:
   inserting an endovascular instrument into a vessel; and
   using said instrument to install a clip having an S-shaped configuration with pointed ends for closing the vessel;
   wherein said instrument comprises an inner torque tube and an outer guide tube having a pair of slots in a distal end thereof, said inner torque tube being disposed within said outer guide tube and rotatable relative thereto; and
   wherein the clip is installed by placing a first portion of the clip in contact with said inner torque tube and a second portion of the clip in contact with said outer guide tube, rotating the inner torque tube relative to the outer guide tube to expand the clip until the pointed ends protrude radially outwardly from the slots of the outer guide tube and penetrate the wall of the vessel, and then allowing the clip to contract and close the vessel.

3. The percutaneous medical procedure according to claim 2, wherein said pointed ends comprise barbs for anchoring the pointed ends in a wall of the vessel.

4. The percutaneous medical procedure according to claim 2, further comprising:
   providing a pusher tube inserted between said inner torque tube and said outer guide tube; and
   using said pusher tube to push the clip out of contact with the inner torque tube and the outer guide tube.

5. A percutaneous medical procedure, comprising:
   inserting an endovascular instrument into a vessel; and
   using said instrument to install a clip having an S-shaped configuration with pointed ends for closing the vessel;
   wherein said instrument comprises an inner torque tube having a groove in a distal end thereof, and an outer guide tube having a pair of slots in a distal end thereof, said inner torque tube being disposed within said outer guide tube and rotatable relative thereto; and
   wherein the clip is installed by placing the clip in said groove at the distal end of said inner torque tube with the pointed ends thereof fit within the slots in the distal end of the outer guide tube, rotating the inner torque tube relative to the outer guide tube to expand the clip until the pointed ends protrude outwardly from the slots in the outer guide tube and penetrate the wall of the vessel, and then allowing the clip to contract and close the vessel.

6. The percutaneous medical procedure according to claim 5, further comprising:
   providing a pusher tube inserted between said inner torque tube and said outer guide tube; and
   using said pusher tube to push the clip out of the groove at the distal end of the inner torque tube and the slots of the outer guide tube.

7. The percutaneous medical procedure according to claim 5, wherein said pointed ends comprise barbs for anchoring the pointed ends in a wall of the vessel.

* * * * *